US005783181A

United States Patent [19]

Browne et al.

[11] Patent Number: 5,783,181
[45] Date of Patent: Jul. 21, 1998

[54] THERAPEUTIC USES OF FUSION PROTEINS BETWEEN MUTANT IL 4/IL13 ANTAGONISTS AND IMMUNOGLOBULINS

[75] Inventors: Michael Joseph Browne, Welwyn Garden, England; Peter Ronald Young, Lawrenceville, N.J.; Allan Richard Shatzman, King of Prussia, Pa.; Kay Elizabeth Murphy, Hertford, England; Conrad Gerald Chapman, Orpington, England; Helen Elizabeth Clinkenbeard, Hertford, England

[73] Assignees: SmithKline Beecham Corporation, Philadelphia, Pa.; SmithKline Beecham p.l.c., Brentford, England

[21] Appl. No.: 470,299

[22] Filed: Jun. 6, 1995

[30] Foreign Application Priority Data

Jul. 29, 1994 [GB] United Kingdom ............... 9415379

[51] Int. Cl.⁶ ................................................. A61K 38/20
[52] U.S. Cl. ............... 424/85.2; 424/85.1; 424/178.1; 424/182.1; 424/179.1; 514/825; 514/856; 514/885

[58] Field of Search ............... 424/85.1, 85.2, 424/178.1, 182.1, 179.1; 514/825, 856, 885

[56] References Cited

U.S. PATENT DOCUMENTS 5,349,053  9/1994  Landolfi et al. ............... 530/387.3

FOREIGN PATENT DOCUMENTS 0396387  11/1990  European Pat. Off..
9101004   1/1991  WIPO.

OTHER PUBLICATIONS

Krese et al. *EMBO* 11(9) 1992, pp.3237–3244.

*Primary Examiner*—Garnette D. Draper
*Attorney, Agent, or Firm*—Alissa M. Eagle; William T. King; Edward T. Lentz

[57] ABSTRACT

A soluble protein having IL4 and/or IL13 antagonist or partial antagonist activity comprises an IL4 mutant or variant fused to least one human immunoglobulin constant domain or fragment thereof.

9 Claims, No Drawings

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 6367 base pairs
( B ) TYPE: nucleic acid
( C ) STRANDEDNESS: double
( D ) TOPOLOGY: circular ( x i ) SEQUENCE DESCRIPTION: SEQ ID NO: 1:

GACGTCGACG GATCGGGAGA TCGGGGATCG ATCCGTCGAC GTACGACTAG TTATTAATAG 60

TAATCAATTA CGGGGTCATT AGTTCATAGC CCATATATGG AGTTCCGCGT TACATAACTT 120

ACGGTAAATG GCCCGCCTGG CTGACCGCCC AACGACCCCC GCCCATTGAC GTCAATAATG 180

ACGTATGTTC CCATAGTAAC GCCAATAGGG ACTTTCCATT GACGTCAATG GGTGGACTAT 240

TTACGGTAAA CTGCCCACTT GGCAGTACAT CAAGTGTATC ATATGCCAAG TACGCCCCCT 300

ATTGACGTCA ATGACGGTAA ATGGCCCGCC TGGCATTATG CCCAGTACAT GACCTTATGG 360

GACTTTCCTA CTTGGCAGTA CATCTACGTA TTAGTCATCG CTATTACCAT GGTGATGCGG 420

TTTTGGCAGT ACATCAATGG GCGTGGATAG CGGTTTGACT CACGGGGATT TCCAAGTCTC 480

CACCCCATTG ACGTCAATGG GAGTTTGTTT TGGCACCAAA ATCAACGGGA CTTTCCAAAA 540

TGTCGTAACA ACTCCGCCCC ATTGACGCAA ATGGGCGGTA GGCGTGTACG GTGGGAGGTC 600

TATATAAGCA GAGCTGGGTA CGTGAACCGT CAGATCGCCT GGAGACGCCA TCGAATTCGG 660

```
TTACCTGCAG ATATCAAGCT AATTCGGTAC CGAGCCCAAA TCGGCCGACA AAACTCACAC    720
ATGCCCACCG TGCCCAGCAC CTGAACTCCT GGGGGGACCG TCAGTCTTCC TCTTCCCCCC    780
AAAACCCAAG GACACCCTCA TGATCTCCCG GACCCCTGAG GTCACATGCG TGGTGGTGGA    840
CGTGAGCCAC GAAGACCCTG AGGTCAAGTT CAACTGGTAC GTGGACGGCG TGGAGGTGCA    900
TAATGCCAAG ACAAAGCCGC GGGAGGAGCA GTACAACAGC ACGTACCGGG TGGTCAGCGT    960
CCTCACCGTC CTGCACCAGG ACTGGCTGAA TGGCAAGGAG TACAAGTGCA AGGTCTCCAA   1020
CAAAGCCCTC CCAGCCCCCA TCGAGAAAAC CATCTCCAAA GCCAAAGGGC AGCCCCGAGA   1080
ACCACAGGTG TACACCCTGC CCCCATCCCG GGATGAGCTG ACCAAGAACC AGGTCAGCCT   1140
GACCTGCCTG GTCAAAGGCT TCTATCCCAG CGACATCGCC GTGGAGTGGG AGAGCAATGG   1200
GCAGCCGGAG AACAACTACA AGACCACGCC TCCCGTGCTG GACTCCGACG GCTCCTTCTT   1260
CCTCTACAGC AAGCTCACCG TGGACAAGAG CAGGTGGCAG CAGGGGAACG TCTTCTCATG   1320
CTCCGTGATG CATGAGGCTC TGCACAACCA CTACACGCAG AAGAGCCTCT CCCTGTCTCC   1380
GGGTAAATGA GTGTAGTCTA GAGCTCGCTG ATCAGCCTCG ACTGTGCCTT CTAGTTGCCA   1440
GCCATCTGTT GTTTGCCCCT CCCCCGTGCC TTCCTTGACC CTGGAAGGTG CCACTCCCAC   1500
TGTCCTTTCC TAATAAAATG AGGAAATTGC ATCGCATTGT CTGAGTAGGT GTCATTCTAT   1560
TCTGGGGGGT GGGGTGGGGC AGGACAGCAA GGGGGAGGAT TGGGAAGACA ATAGCAGGCA   1620
TGCTGGGGAT GCGGTGGGCT CTATGGAACC AGCTGGGGCT CGAGGGGGGA TCTCCCGATC   1680
CCCAGCTTTG CTTCTCAATT TCTTATTTGC ATAATGAGAA AAAAAGGAAA ATTAATTTTA   1740
ACACCAATTC AGTAGTTGAT TGAGCAAATG CGTTGCCAAA AGGATGCTT  TAGAGACAGT   1800
GTTCTCTGCA CAGATAAGGA CAAACATTAT TCAGAGGGAG TACCCAGAGC TGAGACTCCT   1860
AAGCCAGTGA GTGGCACAGC ATTCTAGGGA GAAATATGCT TGTCATCACC GAAGCCTGAT   1920
TCCGTAGAGC CACACCTTGG TAAGGGCCAA TCTGCTCACA CAGGATAGAG AGGGCAGGAG   1980
CCAGGGCAGA GCATATAAGG TGAGGTAGGA TCAGTTGCTC CTCACATTTG CTTCTGACAT   2040
AGTTGTGTTG GGAGCTTGGA TAGCTTGGAC AGCTCAGGGC TGCGATTTCG CGCCAAACTT   2100
GACGGCAATC CTAGCGTGAA GGCTGGTAGG ATTTTATCCC CGCTGCCATC ATGGTTCGAC   2160
CATTGAACTG CATCGTCGCC GTGTCCCAAA ATATGGGGAT TGGCAAGAAC GGAGACCTAC   2220
CCTGGCCTCC GCTCAGGAAC GAGTTCAAGT ACTTCCAAAG AATGACCACA ACCTCTTCAG   2280
TGGAAGGTAA ACAGAATCTG GTGATTATGG GTAGGAAAAC CTGGTTCTCC ATTCCTGAGA   2340
AGAATCGACC TTTAAAGGAC AGAATTAATA TAGTTCTCAG TAGAGAACTC AAAGAACCAC   2400
CACGAGGAGC TCATTTTCTT GCCAAAAGTT TGGATGATGC CTTAAGACTT ATTGAACAAC   2460
CGGAATTGGC AAGTAAAGTA GACATGGTTT GGATAGTCGG AGGCAGTTCT GTTACCAGG   2520
AAGCCATGAA TCAACCAGGC CACCTTAGAC TCTTTGTGAC AAGGATCATG CAGGAATTTG   2580
AAAGTGACAC GTTTTCCCA GAAATTGATT TGGGGAAATA TAAACTTCTC CCAGAATACC    2640
CAGGCGTCCT CTCTGAGGTC CAGGAGGAAA AAGGCATCAA GTATAAGTTT GAAGTCTACG   2700
AGAAGAAAGA CTAACAGGAA GATGCTTTCA AGTTCTCTGC TCCCTCCTA  AAGCTATGCA   2760
TTTTTATAAG ACCATGCTAG CTTGAACTTG TTATTGCAG  CTTATAATGG TTACAAATAA   2820
AGCAATAGCA TCACAAATTT CACAAATAAA GCATTTTTTT CACTGCATTC TAGTTGTGGT   2880
TTGTCCAAAC TCATCAATGT ATCTTATCAT GTCTGGATCA ACGATAGCTT ATCTGTGGGC   2940
GATGCCAAGC ACCTGGATGC TGTTGGTTTC CTGCTACTGA TTTAGAAGCC ATTTGCCCCC   3000
TGAGTGGGGC TTGGGAGCAC TAACTTTCTC TTTCAAAGGA AGCAATGCAG AAAGAAAAGC   3060
```

```
ATACAAAGTA  TAAGCTGCCA  TGTAATAATG  GAAGAAGATA  AGGTTGTATG  AATTAGATTT   3120
ACATACTTCT  GAATTGAAAC  TAAACACCTT  TAAATTCTTA  AATATATAAC  ACATTTCATA   3180
TGAAAGTATT  TTACATAAGT  AACTCAGATA  CATAGAAAAC  AAAGCTAATG  ATAGGTGTCC   3240
CTAAAAGTTC  ATTTATTAAT  TCTACAAATG  ATGAGCTGGC  CATCAAAATT  CCAGCTCAAT   3300
TCTTCAACGA  ATTAGAAAGA  GCAATCTGCA  AACTCATCTG  GAATAACAAA  AAACCTAGGA   3360
TAGCAAAAAC  TCTTCTCAAG  GATAAAAGAA  CCTCTGGTGG  AATCACCATG  CCTGACCTAA   3420
AGCTGTACTA  CAGAGCAATT  GTGATAAAAA  CTGCATGGTA  CTGATATAGA  AACGGACAAG   3480
TAGACCAATG  GAATAGAACC  CACACACCTA  TGGTCACTTG  ATCTTCAACA  AGAGAGCTAA   3540
AACCATCCAC  TGGAAAAAAG  ACAGCATTTT  CAACAAATGG  TGCTGGCACA  ACTGGTGGTT   3600
ATCATGGAGA  AGAATGTGAA  TTGATCCATT  CCAATCTCCT  TGTACTAAGG  TCAAATCTAA   3660
GTGGATCAAG  GAACTCCACA  TAAAACCAGA  GACACTGAAA  CTTATAGAGG  AGAAAGTGGG   3720
GAAAAGCCTC  GAAGATATGG  GCACAGGGGA  AAAATTCCTG  AATAGAACAG  CAATGGCTTG   3780
TGCTGTAAGA  TCGAGAATTG  ACAAATGGGA  CCTCATGAAA  CTCCAAAGCT  ATCGGATCAA   3840
TTCCTCCAAA  AAAGCCTCCT  CACTACTTCT  GGAATAGCTC  AGAGGCCGAG  GCGGCCTCGG   3900
CCTCTGCATA  AATAAAAAAA  ATTAGTCAGC  CATGCATGGG  CGGAGAATG  GGCGGAACTG    3960
GGCGGAGTTA  GGGGCGGGAT  GGGCGGAGTT  AGGGGCGGGA  CTATGGTTGC  TGACTAATTG   4020
AGATGCATGC  TTTGCATACT  TCTGCCTGCT  GGGGAGCCTG  GGACTTTCC   ACACCTGGTT   4080
GCTGACTAAT  TGAGATGCAT  GCTTTGCATA  CTTCTGCCTG  CTGGGGAGCC  TGGGGACTTT   4140
CCACACCCTA  ACTGACACAC  ATTCCACAGA  ATTAATTCCC  GATCCCGTCG  ACCTCGAGAG   4200
CTTGGCGTAA  TCATGGTCAT  AGCTGTTTCC  TGTGTGAAAT  TGTTATCCGC  TCACAATTCC   4260
ACACAACATA  CGAGCCGGAA  GCATAAAGTG  TAAAGCCTGG  GGTGCCTAAT  GAGTGAGCTA   4320
ACTCACATTA  ATTGCGTTGC  GCTCACTGCC  CGCTTTCCAG  TCGGGAAACC  TGTCGTGCCA   4380
GCTGCATTAA  TGAATCGGCC  AACGCGCGGG  GAGAGGCGGT  TTGCGTATTG  GGCGCTCTTC   4440
CGCTTCCTCG  CTCACTGACT  CGCTGCGCTC  GGTCGTTCGG  CTGCGGCGAG  CGGTATCAGC   4500
TCACTCAAAG  GCGGTAATAC  GGTTATCCAC  AGAATCAGGG  GATAACGCAG  GAAAGAACAT   4560
GTGAGCAAAA  GGCCAGCAAA  AGGCCAGGAA  CCGTAAAAAG  GCCGCGTTGC  TGGCGTTTTT   4620
CCATAGGCTC  CGCCCCCCTG  ACGAGCATCA  CAAAAATCGA  CGCTCAAGTC  AGAGGTGGCG   4680
AAACCCGACA  GGACTATAAA  GATACCAGGC  GTTTCCCCCT  GGAAGCTCCC  TCGTGCGCTC   4740
TCCTGTTCCG  ACCCTGCCGC  TTACCGGATA  CCTGTCCGCC  TTTCTCCCTT  CGGGAAGCGT   4800
GGCGCTTTCT  CAATGCTCAC  GCTGTAGGTA  TCTCAGTTCG  GTGTAGGTCG  TTCGCTCCAA   4860
GCTGGGCTGT  GTGCACGAAC  CCCCCGTTCA  GCCCGACCGC  TGCGCCTTAT  CCGGTAACTA   4920
TCGTCTTGAG  TCCAACCCGG  TAAGACACGA  CTTATCGCCA  CTGGCAGCAG  CCACTGGTAA   4980
CAGGATTAGC  AGAGCGAGGT  ATGTAGGCGG  TGCTACAGAG  TTCTTGAAGT  GGTGGCCTAA   5040
CTACGGCTAC  ACTAGAAGGA  CAGTATTTGG  TATCTGCGCT  CTGCTGAAGC  CAGTTACCTT   5100
CGGAAAAAGA  GTTGGTAGCT  CTTGATCCGG  CAAACAAACC  ACCGCTGGTA  GCGGTGGTTT   5160
TTTTGTTTGC  AAGCAGCAGA  TTACGCGCAG  AAAAAAAGGA  TCTCAAGAAG  ATCCTTTGAT   5220
CTTTTCTACG  GGGTCTGACG  CTCAGTGGAA  CGAAAACTCA  CGTTAAGGGA  TTTTGGTCAT   5280
GAGATTATCA  AAAAGGATCT  TCACCTAGAT  CCTTTTAAAT  TAAAAATGAA  GTTTTAAATC   5340
AATCTAAAGT  ATATATGAGT  AAACTTGGTC  TGACAGTTAC  CAATGCTTAA  TCAGTGAGGC   5400
ACCTATCTCA  GCGATCTGTC  TATTTCGTTC  ATCCATAGTT  GCCTGACTCC  CCGTCGTGTA   5460
```

```
GATAACTACG ATACGGGAGG GCTTACCATC TGGCCCCAGT GCTGCAATGA TACCGCGAGA      5520

CCCACGCTCA CCGGCTCCAG ATTTATCAGC AATAAACCAG CCAGCCGGAA GGGCCGAGCG      5580

CAGAAGTGGT CCTGCAACTT TATCCGCCTC CATCCAGTCT ATTAATTGTT GCCGGGAAGC      5640

TAGAGTAAGT AGTTCGCCAG TTAATAGTTT GCGCAACGTT GTTGCCATTG CTACAGGCAT      5700

CGTGGTGTCA CGCTCGTCGT TTGGTATGGC TTCATTCAGC TCCGGTTCCC AACGATCAAG      5760

GCGAGTTACA TGATCCCCCA TGTTGTGCAA AAAAGCGGTT AGCTCCTTCG GTCCTCCGAT      5820

CGTTGTCAGA AGTAAGTTGG CCGCAGTGTT ATCACTCATG GTTATGGCAG CACTGCATAA      5880

TTCTCTTACT GTCATGCCAT CCGTAAGATG CTTTTCTGTG ACTGGTGAGT ACTCAACCAA      5940

GTCATTCTGA GAATAGTGTA TGCGGCGACC GAGTTGCTCT TGCCCGGCGT CAATACGGGA      6000

TAATACCGCG CCACATAGCA GAACTTTAAA AGTGCTCATC ATTGGAAAAC GTTCTTCGGG      6060

GCGAAAACTC TCAAGGATCT TACCGCTGTT GAGATCCAGT TCGATGTAAC CCACTCGTGC      6120

ACCCAACTGA TCTTCAGCAT CTTTTACTTT CACCAGCGTT TCTGGGTGAG CAAAAACAGG      6180

AAGGCAAAAT GCCGCAAAAA AGGGAATAAG GGCGACACGG AAATGTTGAA TACTCATACT      6240

CTTCCTTTTT CAATATTATT GAAGCATTTA TCAGGGTTAT TGTCTCATGA GCGGATACAT      6300

ATTTGAATGT ATTTAGAAAA ATAAACAAAT AGGGGTTCCG CGCACATTTC CCCGAAAAGT      6360

GCCACCT                                                              6367

( 2 ) INFORMATION FOR SEQ ID NO: 2:

( i ) SEQUENCE CHARACTERISTICS:
           ( A ) LENGTH: 6926 base pairs
           ( B ) TYPE: nucleic acid
           ( C ) STRANDEDNESS: double
           ( D ) TOPOLOGY: circular ( x i ) SEQUENCE DESCRIPTION: SEQ ID NO: 2:

GACGTCGACG GATCGGGAGA TCGGGGATCG ATCCGTCGAC GTACGACTAG TTATTAATAG       60

TAATCAATTA CGGGGTCATT AGTTCATAGC CCATATATGG AGTTCCGCGT TACATAACTT      120

ACGGTAAATG GCCCGCCTGG CTGACCGCCC AACGACCCCC GCCCATTGAC GTCAATAATG      180

ACGTATGTTC CCATAGTAAC GCCAATAGGG ACTTTCCATT GACGTCAATG GGTGGACTAT      240

TTACGGTAAA CTGCCCACTT GGCAGTACAT CAAGTGTATC ATATGCCAAG TACGCCCCCT      300

ATTGACGTCA ATGACGGTAA ATGGCCCGCC TGGCATTATG CCCAGTACAT GACCTTATGG      360

GACTTTCCTA CTTGGCAGTA CATCTACGTA TTAGTCATCG CTATTACCAT GGTGATGCGG      420

TTTTGGCAGT ACATCAATGG GCGTGGATAG CGGTTTGACT CACGGGGATT TCCAAGTCTC      480

CACCCCATTG ACGTCAATGG GAGTTTGTTT TGGCACCAAA ATCAACGGGA CTTTCCAAAA      540

TGTCGTAACA ACTCCGCCCC ATTGACGCAA ATGGGCGGTA GGCGTGTACG GTGGGAGGTC      600

TATATAAGCA GAGCTGGGTA CGTGAACCGT CAGATCGCCT GGAGACGCCA TCGAATTCGG      660

TTACCTGCAG ATGGGCTGCA GGAATTCCGC ATTGCAGAGA TAATTGTATT TAAGTGCCTA      720

GCTCGATACA ATAAACGCCA TTTGACCATT CACCACATTG GTGTGCACCT CCAAGCTTAC      780

CTGCCATGGG TCTCACCTCC CAACTGCTTC CCCCTCTGTT CTTCCTGCTA GCATGTGCCG      840

GCAACTTTGT CCACGGACAC AAGTGCGATA TCACCTTACA GGAGATCATC AAAACTTTGA      900

ACAGCCTCAC AGAGCAGAAG ACTCTGTGCA CCGAGTTGAC CGTAACAGAC ATCTTTGCTG      960

CCTCCAAGAA CACAACTGAG AAGGAAACCT TCTGCAGGGC TGCGACTGTG CTCCGGCAGT     1020

TCTACAGCCA CCATGAGAAG GACACTCGCT GCCTGGGTGC GACTGCACAG CAGTTCCACA     1080
```

| | | | | | |
|---|---|---|---|---|---|
| GGCACAAGCA | GCTGATCCGA | TTCCTGAAAC | GGCTCGACAG | GAACCTCTGG | GGCCTGGCGG | 1140 |
| GCTTGAATTC | CTGTCCTGTG | AAGGAAGCCA | ACCAGAGTAC | GTTGGAAAAC | TTCTTGGAAA | 1200 |
| GGCTAAAGAC | GATCATGAGA | GAGAAAGACT | CAAAGTGTTC | GAGCGGTACC | GAGCCCAAAT | 1260 |
| CGGCCGACAA | AACTCACACA | TGCCCACCGT | GCCCAGCACC | TGAACTCCTG | GGGGGACCGT | 1320 |
| CAGTCTTCCT | CTTCCCCCCA | AAACCCAAGG | ACACCCTCAT | GATCTCCCGG | ACCCCTGAGG | 1380 |
| TCACATGCGT | GGTGGTGGAC | GTGAGCCACG | AAGACCCTGA | GGTCAAGTTC | AACTGGTACG | 1440 |
| TGGACGGCGT | GGAGGTGCAT | AATGCCAAGA | CAAAGCCGCG | GGAGGAGCAG | TACAACAGCA | 1500 |
| CGTACCGGGT | GGTCAGCGTC | CTCACCGTCC | TGCACCAGGA | CTGGCTGAAT | GGCAAGGAGT | 1560 |
| ACAAGTGCAA | GGTCTCCAAC | AAAGCCCTCC | CAGCCCCCAT | CGAGAAAACC | ATCTCCAAAG | 1620 |
| CCAAAGGGCA | GCCCCGAGAA | CCACAGGTGT | ACACCCTGCC | CCATCCCGG | GATGAGCTGA | 1680 |
| CCAAGAACCA | GGTCAGCCTG | ACCTGCCTGG | TCAAAGGCTT | CTATCCCAGC | GACATCGCCG | 1740 |
| TGGAGTGGGA | GAGCAATGGG | CAGCCGGAGA | ACAACTACAA | GACCACGCCT | CCCGTGCTGG | 1800 |
| ACTCCGACGG | CTCCTTCTTC | CTCTACAGCA | AGCTCACCGT | GGACAAGAGC | AGGTGGCAGC | 1860 |
| AGGGGAACGT | CTTCTCATGC | TCCGTGATGC | ATGAGGCTCT | GCACAACCAC | TACACGCAGA | 1920 |
| AGAGCCTCTC | CCTGTCTCCG | GGTAAATGAG | TGTAGTCTAG | AGCTCGCTGA | TCAGCCTCGA | 1980 |
| CTGTGCCTTC | TAGTTGCCAG | CCATCTGTTG | TTTGCCCCTC | CCCCGTGCCT | TCCTTGACCC | 2040 |
| TGGAAGGTGC | CACTCCCACT | GTCCTTTCCT | AATAAAATGA | GGAAATTGCA | TCGCATTGTC | 2100 |
| TGAGTAGGTG | TCATTCTATT | CTGGGGGGTG | GGGTGGGGCA | GGACAGCAAG | GGGGAGGATT | 2160 |
| GGGAAGACAA | TAGCAGGCAT | GCTGGGGATG | CGGTGGGCTC | TATGGAACCA | GCTGGGGCTC | 2220 |
| GAGGGGGGAT | CTCCCGATCC | CCAGCTTTGC | TTCTCAATTT | CTTATTTGCA | TAATGAGAAA | 2280 |
| AAAAGGAAAA | TTAATTTTAA | CACCAATTCA | GTAGTTGATT | GAGCAAATGC | GTTGCCAAAA | 2340 |
| AGGATGCTTT | AGAGACAGTG | TTCTCTGCAC | AGATAAGGAC | AAACATTATT | CAGAGGGAGT | 2400 |
| ACCCAGAGCT | GAGACTCCTA | AGCCAGTGAG | TGGCACAGCA | TTCTAGGGAG | AAATATGCTT | 2460 |
| GTCATCACCG | AAGCCTGATT | CCGTAGAGCC | ACACCTTGGT | AAGGGCCAAT | CTGCTCACAC | 2520 |
| AGGATAGAGA | GGGCAGGAGC | CAGGGCAGAG | CATATAAGGT | GAGGTAGGAT | CAGTTGCTCC | 2580 |
| TCACATTTGC | TTCTGACATA | GTTGTGTTGG | GAGCTTGGAT | AGCTTGGACA | GCTCAGGGCT | 2640 |
| GCGATTTCGC | GCCAAACTTG | ACGGCAATCC | TAGCGTGAAG | GCTGGTAGGA | TTTTATCCCC | 2700 |
| GCTGCCATCA | TGGTTCGACC | ATTGAACTGC | ATCGTCGCCG | TGTCCCAAAA | TATGGGGATT | 2760 |
| GGCAAGAACG | GAGACCTACC | CTGGCCTCCG | CTCAGGAACG | AGTTCAAGTA | CTTCCAAAGA | 2820 |
| ATGACCACAA | CCTCTTCAGT | GGAAGGTAAA | CAGAATCTGG | TGATTATGGG | TAGGAAAACC | 2880 |
| TGGTTCTCCA | TTCCTGAGAA | GAATCGACCT | TTAAAGGACA | GAATTAATAT | AGTTCTCAGT | 2940 |
| AGAGAACTCA | AAGAACCACC | ACGAGGAGCT | CATTTTCTTG | CCAAAAGTTT | GGATGATGCC | 3000 |
| TTAAGACTTA | TTGAACAACC | GGAATTGGCA | AGTAAAGTAG | ACATGGTTTG | GATAGTCGGA | 3060 |
| GGCAGTTCTG | TTTACCAGGA | AGCCATGAAT | CAACCAGGCC | ACCTTAGACT | CTTTGTGACA | 3120 |
| AGGATCATGC | AGGAATTTGA | AAGTGACACG | TTTTTCCCAG | AAATTGATTT | GGGGAAATAT | 3180 |
| AAACTTCTCC | CAGAATACCC | AGGCGTCCTC | TCTGAGGTCC | AGGAGGAAAA | AGGCATCAAG | 3240 |
| TATAAGTTTG | AAGTCTACGA | GAAGAAAGAC | TAACAGGAAG | ATGCTTTCAA | GTTCTCTGCT | 3300 |
| CCCCTCCTAA | AGCTATGCAT | TTTTATAAGA | CCATGCTAGC | TTGAACTTGT | TTATTGCAGC | 3360 |
| TTATAATGGT | TACAAATAAA | GCAATAGCAT | CACAAATTTC | ACAAATAAAG | CATTTTTTTC | 3420 |
| ACTGCATTCT | AGTTGTGGTT | TGTCCAAACT | CATCAATGTA | TCTTATCATG | TCTGGATCAA | 3480 |

-continued

| | | | | | | |
|---|---|---|---|---|---|---|
| CGATAGCTTA | TCTGTGGGCG | ATGCCAAGCA | CCTGGATGCT | GTTGGTTTCC | TGCTACTGAT | 3540 |
| TTAGAAGCCA | TTTGCCCCCT | GAGTGGGGCT | TGGGAGCACT | AACTTTCTCT | TTCAAAGGAA | 3600 |
| GCAATGCAGA | AAGAAAAGCA | TACAAAGTAT | AAGCTGCCAT | GTAATAATGG | AAGAAGATAA | 3660 |
| GGTTGTATGA | ATTAGATTTA | CATACTTCTG | AATTGAAACT | AAACACCTTT | AAATTCTTAA | 3720 |
| ATATATAACA | CATTTCATAT | GAAAGTATTT | TACATAAGTA | ACTCAGATAC | ATAGAAAACA | 3780 |
| AAGCTAATGA | TAGGTGTCCC | TAAAAGTTCA | TTATTAATT | CTACAAATGA | TGAGCTGGCC | 3840 |
| ATCAAAATTC | CAGCTCAATT | CTTCAACGAA | TTAGAAAGAG | CAATCTGCAA | ACTCATCTGG | 3900 |
| AATAACAAAA | AACCTAGGAT | AGCAAAAACT | CTTCTCAAGG | ATAAAGAAC | CTCTGGTGGA | 3960 |
| ATCACCATGC | CTGACCTAAA | GCTGTACTAC | AGAGCAATTG | TGATAAAAAC | TGCATGGTAC | 4020 |
| TGATATAGAA | ACGGACAAGT | AGACCAATGG | AATAGAACCC | ACACACCTAT | GGTCACTTGA | 4080 |
| TCTTCAACAA | GAGAGCTAAA | ACCATCCACT | GGAAAAAGA | CAGCATTTTC | AACAAATGGT | 4140 |
| GCTGGCACAA | CTGGTGGTTA | TCATGGAGAA | GAATGTGAAT | TGATCCATTC | CAATCTCCTT | 4200 |
| GTACTAAGGT | CAAATCTAAG | TGGATCAAGG | AACTCCACAT | AAAACCAGAG | ACACTGAAAC | 4260 |
| TTATAGAGGA | GAAAGTGGGG | AAAAGCCTCG | AAGATATGGG | CACAGGGGAA | AAATTCCTGA | 4320 |
| ATAGAACAGC | AATGGCTTGT | GCTGTAAGAT | CGAGAATTGA | CAAATGGGAC | CTCATGAAAC | 4380 |
| TCCAAAGCTA | TCGGATCAAT | TCCTCCAAAA | AAGCCTCCTC | ACTACTTCTG | GAATAGCTCA | 4440 |
| GAGGCCGAGG | CGGCCTCGGC | CTCTGCATAA | ATAAAAAAAA | TTAGTCAGCC | ATGCATGGGG | 4500 |
| CGGAGAATGG | GCGGAACTGG | GCGGAGTTAG | GGGCGGGATG | GGCGGAGTTA | GGGGCGGGAC | 4560 |
| TATGGTTGCT | GACTAATTGA | GATGCATGCT | TTGCATACTT | CTGCCTGCTG | GGGAGCCTGG | 4620 |
| GGACTTTCCA | CACCTGGTTG | CTGACTAATT | GAGATGCATG | CTTTGCATAC | TTCTGCCTGC | 4680 |
| TGGGGAGCCT | GGGGACTTTC | CACACCCTAA | CTGACACACA | TTCCACAGAA | TTAATTCCCG | 4740 |
| ATCCCGTCGA | CCTCGAGAGC | TTGGCGTAAT | CATGGTCATA | GCTGTTTCCT | GTGTGAAATT | 4800 |
| GTTATCCGCT | CACAATTCCA | CACAACATAC | GAGCCGGAAG | CATAAAGTGT | AAAGCCTGGG | 4860 |
| GTGCCTAATG | AGTGAGCTAA | CTCACATTAA | TTGCGTTGCG | CTCACTGCCC | GCTTTCCAGT | 4920 |
| CGGGAAACCT | GTCGTGCCAG | CTGCATTAAT | GAATCGGCCA | ACGCGCGGGG | AGAGGCGGTT | 4980 |
| TGCGTATTGG | GCGCTCTTCC | GCTTCCTCGC | TCACTGACTC | GCTGCGCTCG | GTCGTTCGGC | 5040 |
| TGCGGCGAGC | GGTATCAGCT | CACTCAAAGG | CGGTAATACG | GTTATCCACA | GAATCAGGGG | 5100 |
| ATAACGCAGG | AAAGAACATG | TGAGCAAAAG | GCCAGCAAAA | GGCCAGGAAC | CGTAAAAAGG | 5160 |
| CCGCGTTGCT | GGCGTTTTTC | CATAGGCTCC | GCCCCCCTGA | CGAGCATCAC | AAAAATCGAC | 5220 |
| GCTCAAGTCA | GAGGTGGCGA | AACCCGACAG | GACTATAAAG | ATACCAGGCG | TTTCCCCCTG | 5280 |
| GAAGCTCCCT | CGTGCGCTCT | CCTGTTCCGA | CCCTGCCGCT | TACCGGATAC | CTGTCCGCCT | 5340 |
| TTCTCCCTTC | GGGAAGCGTG | GCGCTTTCTC | AATGCTCACG | CTGTAGGTAT | CTCAGTTCGG | 5400 |
| TGTAGGTCGT | TCGCTCCAAG | CTGGGCTGTG | TGCACGAACC | CCCCGTTCAG | CCCGACCGCT | 5460 |
| GCGCCTTATC | CGGTAACTAT | CGTCTTGAGT | CCAACCCGGT | AAGACACGAC | TTATCGCCAC | 5520 |
| TGGCAGCAGC | CACTGGTAAC | AGGATTAGCA | GAGCGAGGTA | TGTAGGCGGT | GCTACAGAGT | 5580 |
| TCTTGAAGTG | GTGGCCTAAC | TACGGCTACA | CTAGAAGGAC | AGTATTTGGT | ATCTGCGCTC | 5640 |
| TGCTGAAGCC | AGTTACCTTC | GGAAAAAGAG | TTGGTAGCTC | TTGATCCGGC | AAACAAACCA | 5700 |
| CCGCTGGTAG | CGGTGGTTTT | TTTGTTTGCA | AGCAGCAGAT | TACGCGCAGA | AAAAAAGGAT | 5760 |
| CTCAAGAAGA | TCCTTTGATC | TTTTCTACGG | GGTCTGACGC | TCAGTGGAAC | GAAAACTCAC | 5820 |
| GTTAAGGGAT | TTTGGTCATG | AGATTATCAA | AAAGGATCTT | CACCTAGATC | CTTTTAAATT | 5880 |

-continued

```
AAAAATGAAG TTTTAAATCA ATCTAAAGTA TATATGAGTA AACTTGGTCT GACAGTTACC    5940
AATGCTTAAT CAGTGAGGCA CCTATCTCAG CGATCTGTCT ATTTCGTTCA TCCATAGTTG    6000
CCTGACTCCC CGTCGTGTAG ATAACTACGA TACGGGAGGG CTTACCATCT GGCCCCAGTG    6060
CTGCAATGAT ACCGCGAGAC CCACGCTCAC CGGCTCCAGA TTTATCAGCA ATAAACCAGC    6120
CAGCCGGAAG GGCCGAGCGC AGAAGTGGTC CTGCAACTTT ATCCGCCTCC ATCCAGTCTA    6180
TTAATTGTTG CCGGGAAGCT AGAGTAAGTA GTTCGCCAGT TAATAGTTTG CGCAACGTTG    6240
TTGCCATTGC TACAGGCATC GTGGTGTCAC GCTCGTCGTT TGGTATGGCT TCATTCAGCT    6300
CCGGTTCCCA ACGATCAAGG CGAGTTACAT GATCCCCCAT GTTGTGCAAA AAAGCGGTTA    6360
GCTCCTTCGG TCCTCCGATC GTTGTCAGAA GTAAGTTGGC CGCAGTGTTA TCACTCATGG    6420
TTATGGCAGC ACTGCATAAT TCTCTTACTG TCATGCCATC CGTAAGATGC TTTTCTGTGA    6480
CTGGTGAGTA CTCAACCAAG TCATTCTGAG AATAGTGTAT GCGGCGACCG AGTTGCTCTT    6540
GCCCGGCGTC AATACGGGAT AATACCGCGC CACATAGCAG AACTTTAAAA GTGCTCATCA    6600
TTGGAAAACG TTCTTCGGGG CGAAAACTCT CAAGGATCTT ACCGCTGTTG AGATCCAGTT    6660
CGATGTAACC CACTCGTGCA CCCAACTGAT CTTCAGCATC TTTTACTTTC ACCAGCGTTT    6720
CTGGGTGAGC AAAAACAGGA AGGCAAAATG CCGCAAAAAA GGGAATAAGG GCGACACGGA    6780
AATGTTGAAT ACTCATACTC TTCCTTTTTC AATATTATTG AAGCATTTAT CAGGGTTATT    6840
GTCTCATGAG CGGATACATA TTTGAATGTA TTTAGAAAAA TAAACAAATA GGGGTTCCGC    6900
GCACATTTCC CCGAAAAGTG CCACCT                                         6926
```

( 2 ) INFORMATION FOR SEQ ID NO: 3:

( i ) SEQUENCE CHARACTERISTICS:
        ( A ) LENGTH: 1164 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 3:

```
ATGGGTCTCA CCTCCCAACT GCTTCCCCCT CTGTTCTTCC TGCTAGCATG TGCCGGCAAC      60
TTTGTCCACG GACACAAGTG CGATATCACC TTACAGGAGA TCATCAAAAC TTTGAACAGC     120
CTCACAGAGC AGAAGACTCT GTGCACCGAG TTGACCGTAA CAGACATCTT TGCTGCCTCC     180
AAGAACACAA CTGAGAAGGA AACCTTCTGC AGGGCTGCGA CTGTGCTCCG GCAGTTCTAC     240
AGCCACCATG AGAAGGACAC TCGCTGCCTG GGTGCGACTG CACAGCAGTT CCACAGGCAC     300
AAGCAGCTGA TCCGATTCCT GAAACGGCTC GACAGGAACC TCTGGGGCCT GGCGGGCTTG     360
AATTCCTGTC CTGTGAAGGA AGCCAACCAG AGTACGTTGG AAAACTTCTT GGAAAGGCTA     420
AAGACGATCA TGAGAGAGAA AGACTCAAAG TGTTCGAGCG GTACCGAGCC CAAATCGGCC     480
GACAAAACTC ACACATGCCC ACCGTGCCCA GCACCTGAAC TCCTGGGGGG ACCGTCAGTC     540
TTCCTCTTCC CCCCAAAACC CAAGGACACC CTCATGATCT CCCGGACCCC TGAGGTCACA     600
TGCGTGGTGG TGGACGTGAG CCACGAAGAC CCTGAGGTCA AGTTCAACTG GTACGTGGAC     660
GGCGTGGAGG TGCATAATGC CAAGACAAAG CCGCGGGAGG AGCAGTACAA CAGCACGTAC     720
CGGGTGGTCA GCGTCCTCAC CGTCCTGCAC CAGGACTGGC TGAATGGCAA GGAGTACAAG     780
TGCAAGGTCT CCAACAAAGC CCTCCCAGCC CCCATCGAGA AAACCATCTC CAAAGCCAAA     840
GGGCAGCCCC GAGAACCACA GGTGTACACC CTGCCCCCAT CCCGGGATGA GCTGACCAAG     900
AACCAGGTCA GCCTGACCTG CCTGGTCAAA GGCTTCTATC CCAGCGACAT CGCCGTGGAG     960
TGGGAGAGCA ATGGGCAGCC GGAGAACAAC TACAAGACCA CGCCTCCCGT GCTGGACTCC    1020
```

```
GACGGCTCCT TCTTCCTCTA CAGCAAGCTC ACCGTGGACA AGAGCAGGTG GCAGCAGGGG    1080

AACGTCTTCT CATGCTCCGT GATGCATGAG GCTCTGCACA ACCACTACAC GCAGAAGAGC    1140

CTCTCCCTGT CTCCGGGTAA ATGA                                          1164
```

( 2 ) INFORMATION FOR SEQ ID NO: 4:

( i ) SEQUENCE CHARACTERISTICS:
        ( A ) LENGTH: 387 amino acids
        ( B ) TYPE: amino acid
        ( C ) STRANDEDNESS:
        ( D ) TOPOLOGY: linear ( x i ) SEQUENCE DESCRIPTION: SEQ ID NO: 4:

```
Met Gly Leu Thr Ser Gln Leu Leu Pro Pro Leu Phe Phe Leu Leu Ala
 1           5                   10                  15
Cys Ala Gly Asn Phe Val His Gly His Lys Cys Asp Ile Thr Leu Gln
            20                  25                  30
Glu Ile Ile Lys Thr Leu Asn Ser Leu Thr Glu Gln Lys Thr Leu Cys
            35                  40                  45
Thr Glu Leu Thr Val Thr Asp Ile Phe Ala Ala Ser Lys Asn Thr Thr
50                  55                  60
Glu Lys Glu Thr Phe Cys Arg Ala Ala Thr Val Leu Arg Gln Phe Tyr
65                  70                  75                  80
Ser His His Glu Lys Asp Thr Arg Cys Leu Gly Ala Thr Ala Gln Gln
                85                  90                  95
Phe His Arg His Lys Gln Leu Ile Arg Phe Leu Lys Arg Leu Asp Arg
            100                 105                 110
Asn Leu Trp Gly Leu Ala Gly Leu Asn Ser Cys Pro Val Lys Glu Ala
            115                 120                 125
Asn Gln Ser Thr Leu Glu Asn Phe Leu Glu Arg Leu Lys Thr Ile Met
        130                 135                 140
Arg Glu Lys Asp Ser Lys Cys Ser Ser Gly Thr Glu Pro Lys Ser Ala
145                 150                 155                 160
Asp Lys Thr His Thr Cys Pro Pro Cys Pro Ala Pro Glu Leu Leu Gly
                165                 170                 175
Gly Pro Ser Val Phe Leu Phe Pro Pro Lys Pro Lys Asp Thr Leu Met
            180                 185                 190
Ile Ser Arg Thr Pro Glu Val Thr Cys Val Val Val Asp Val Ser His
            195                 200                 205
Glu Asp Pro Glu Val Lys Phe Asn Trp Tyr Val Asp Gly Val Glu Val
        210                 215                 220
His Asn Ala Lys Thr Lys Pro Arg Glu Glu Gln Tyr Asn Ser Thr Tyr
225                 230                 235                 240
Arg Val Val Ser Val Leu Thr Val Leu His Gln Asp Trp Leu Asn Gly
                245                 250                 255
Lys Glu Tyr Lys Cys Lys Val Ser Asn Lys Ala Leu Pro Ala Pro Ile
            260                 265                 270
Glu Lys Thr Ile Ser Lys Ala Lys Gly Gln Pro Arg Glu Pro Gln Val
            275                 280                 285
Tyr Thr Leu Pro Pro Ser Arg Asp Glu Leu Thr Lys Asn Gln Val Ser
        290                 295                 300
Leu Thr Cys Leu Val Lys Gly Phe Tyr Pro Ser Asp Ile Ala Val Glu
305                 310                 315                 320
Trp Glu Ser Asn Gly Gln Pro Glu Asn Asn Tyr Lys Thr Thr Pro Pro
                325                 330                 335
```

| | | | | | | | | | | | | | | |
|---|---|---|---|---|---|---|---|---|---|---|---|---|---|---|
| Val | Leu | Asp | Ser | Asp | Gly | Ser | Phe | Phe | Leu | Tyr | Ser | Lys | Leu | Thr | Val |
| | | | 340 | | | | | 345 | | | | | 350 | | |
| Asp | Lys | Ser | Arg | Trp | Gln | Gln | Gly | Asn | Val | Phe | Ser | Cys | Ser | Val | Met |
| | | 355 | | | | | 360 | | | | | 365 | | | |
| His | Glu | Ala | Leu | His | Asn | His | Tyr | Thr | Gln | Lys | Ser | Leu | Ser | Leu | Ser |
| | 370 | | | | | 375 | | | | | 380 | | | | |
| Pro | Gly | Lys | | | | | | | | | | | | | |
| 385 | | | | | | | | | | | | | | | |

( 2 ) INFORMATION FOR SEQ ID NO: 5:

( i ) SEQUENCE CHARACTERISTICS:
        ( A ) LENGTH: 1006 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 5:

```
GCTTCCACCA AGGGCCCATC CGTCTTCCCC CTGGCGCCCT GCTCCAGGAG CACCTCCGAG      60
AGCACAGCCG CCCTGGGCTG CCTGGTCAAG GACTACTTCC CCGAACCGGT GACGGTGTCG     120
TGGAACTCAG GCGCCCTGAC CAGCGGCGTG CACACCTTCC CGGCTGTCCT ACAGTCCTCA     180
GGACTCTACT CCCTCAGCAG CGTGGTGACC GTGCCCTCCA GCAGCTTGGG CACGAAGACC     240
TACACCTGCA ACGTAGATCA CAAGCCCAGC AACACCAAGG TGGACAAGAG AGTTGAGTCC     300
AAATATGGTC CCCCATGCCC ATCATGCCCA GCACCTGAAT TCCTGGGGGG ACCATCAGTC     360
TTCCTGTTCC CCCCAAAACC CAAGGACACT CTCATGATCT CCCGGACCCC TGAGGTCACG     420
TGCGTGGTGG TGGACGTGAG CCAGGAAGAC CCCGAGGTCC AGTTCAACTG GTACGTGGAT     480
GGCGTGGAGG TGCATAATGC CAAGACAAAG CCGCGGGAGG AGCAGTTCAA CAGCACGTAC     540
CGTGTGGTCA GCGTCCTCAC CGTCCTGCAC CAGGACTGGC TGAACGGCAA GGAGTACAAG     600
TGCAAGGTCT CCAACAAAGG CCTCCCGTCA TCGATCGAGA AAACCATCTC CAAAGCCAAA     660
GGGCAGCCCC GAGAGCCACA GGTGTACACC CTGCCCCCAT CCCAGGAGGA GATGACCAAG     720
AACCAGGTCA GCCTGACCTG CCTGGTCAAA GGCTTCTACC CCAGCGACAT CGCCGTGGAG     780
TGGGAGAGCA ATGGGCAGCC GGAGAACAAC TACAAGACCA CGCCTCCCGT GCTGGACTCC     840
GACGGATCCT TCTTCCTCTA CAGCAGGCTA ACCGTGGACA AGAGCAGGTG GCAGGAGGGG     900
AATGTCTTCT CATGCTCCGT GATGCATGAG GCTCTGCACA ACCACTACAC ACAGAAGAGC     960
CTCTCCCTGT CTCTGGGTAA ATGAGTGTAG TCTAGATCTA CGTATG                  1006
```

( 2 ) INFORMATION FOR SEQ ID NO: 6:

( i ) SEQUENCE CHARACTERISTICS:
        ( A ) LENGTH: 1149 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 6:

```
ATGGGTCTCA CCTCCCAACT GCTTCCCCCT CTGTTCTTCC TGCTAGCATG TGCCGGCAAC      60
TTTGTCCACG GACACAAGTG CGATATCACC TTACAGGAGA TCATCAAAAC TTTGAACAGC     120
CTCACAGAGC AGAAGACTCT GTGCACCGAG TTGACCGTAA CAGACATCTT TGCTGCCTCC     180
AAGAACACAA CTGAGAAGGA AACCTTCTGC AGGGCTGCGA CTGTGCTCCG GCAGTTCTAC     240
AGCCACCATG AGAAGGACAC TCGCTGCCTG GGTGCGACTG CACAGCAGTT CCACAGGCAC     300
AAGCAGCTGA TCCGATTCCT GAAACGGCTC GACAGGAACC TCTGGGGCCT GGCGGGCTTG     360
```

```
AATTCCTGTC CTGTGAAGGA AGCCAACCAG AGTACGTTGG AAAACTTCTT GGAAAGGCTA    420
AAGACGATCA TGAGAGAGAA AGACTCAAAG TGCTCGAGCG AGTCCAAATA TGGTCCCCCA    480
TGCCCATCAT GCCCAGCACC TGAATTTCTG GGGGGACCAT CAGTCTTCCT GTTCCCCCCA    540
AAACCCAAGG ACACTCTCAT GATCTCCCGG ACCCCTGAGG TCACGTGCGT GGTGGTGGAC    600
GTGAGCCAGG AAGACCCCGA GGTCCAGTTC AACTGGTACG TGGATGGCGT GGAGGTGCAT    660
AATGCCAAGA CAAAGCCGCG GGAGGAGCAG TTCAACAGCA CGTACCGTGT GGTCAGCGTC    720
CTCACCGTCC TGCACCAGGA CTGGCTGAAC GGCAAGGAGT ACAAGTGCAA GGTCTCCAAC    780
AAAGGCCTCC CGTCATCGAT CGAGAAAACC ATCTCCAAAG CCAAAGGGCA GCCCCGAGAG    840
CCACAGGTGT ACACCCTGCC CCCATCCCAG GAGGAGATGA CCAAGAACCA GGTCAGCCTG    900
ACCTGCCTGG TCAAAGGCTT CTACCCCAGC GACATCGCCG TGGAGTGGGA GAGCAATGGG    960
CAGCCGGAGA ACAACTACAA GACCACGCCT CCCGTGCTGG ACTCCGACGG ATCCTTCTTC    1020
CTCTACAGCA GGCTAACCGT GGACAAGAGC AGGTGGCAGG AGGGGAATGT CTTCTCATGC    1080
TCCGTGATGC ATGAGGCTCT GCACAACCAC TACACACAGA AGAGCCTCTC CCTGTCTCTG    1140
GGTAAATGA                                                            1149
```

(2) INFORMATION FOR SEQ ID NO: 7:

(i) SEQUENCE CHARACTERISTICS:
        (A) LENGTH: 382 amino acids
        (B) TYPE: amino acid
        (C) STRANDEDNESS:
        (D) TOPOLOGY: linear (xi) SEQUENCE DESCRIPTION: SEQ ID NO: 7:

```
Met Gly Leu Thr Ser Gln Leu Leu Pro Pro Leu Phe Phe Leu Leu Ala
 1               5                  10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
 50                  55                  60

Glu Lys Glu Thr Phe Cys Arg Ala Ala Thr Val Leu Arg Gln Phe Tyr
 65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
130                 135                 140

Arg Glu Lys Asp Ser Lys Cys Ser Ser Glu Ser Lys Tyr Gly Pro Pro
145                 150                 155                 160

Cys Pro Ser Cys Pro Ala Pro Glu Phe Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser Gln Glu Asp Pro Glu Val
        195                 200                 205

Gln Phe Asn Trp Tyr Val Asp Gly Val Glu Val His Asn Ala Lys Thr
```

|       |       |       |       |       | 210   |       |       |       |       | 215   |       |       |       |       | 220   |       |       |       |       |
|-------|-------|-------|-------|-------|-------|-------|-------|-------|-------|-------|-------|-------|-------|-------|-------|-------|-------|-------|-------|
| Lys 225 | Pro | Arg | Glu | Glu | Gln 230 | Phe | Asn | Ser | Thr | Tyr 235 | Arg | Val | Val | Ser | Val 240 |
| Leu | Thr | Val | Leu | His 245 | Gln | Asp | Trp | Leu | Asn 250 | Gly | Lys | Glu | Tyr | Lys 255 | Cys |
| Lys | Val | Ser | Asn 260 | Lys | Gly | Leu | Pro | Ser 265 | Ser | Ile | Glu | Lys | Thr 270 | Ile | Ser |
| Lys | Ala | Lys 275 | Gly | Gln | Pro | Arg | Glu 280 | Pro | Gln | Val | Tyr | Thr 285 | Leu | Pro | Pro |
| Ser | Gln 290 | Glu | Glu | Met | Thr | Lys 295 | Asn | Gln | Val | Ser | Leu 300 | Thr | Cys | Leu | Val |
| Lys 305 | Gly | Phe | Tyr | Pro | Ser 310 | Asp | Ile | Ala | Val | Glu 315 | Trp | Glu | Ser | Asn | Gly 320 |
| Gln | Pro | Glu | Asn | Asn 325 | Tyr | Lys | Thr | Thr | Pro 330 | Pro | Val | Leu | Asp | Ser 335 | Asp |
| Gly | Ser | Phe | Phe 340 | Leu | Tyr | Ser | Arg | Leu 345 | Thr | Val | Asp | Lys | Ser 350 | Arg | Trp |
| Gln | Glu | Gly 355 | Asn | Val | Phe | Ser | Cys 360 | Ser | Val | Met | His | Glu 365 | Ala | Leu | His |
| Asn | His 370 | Tyr | Thr | Gln | Lys | Ser 375 | Leu | Ser | Leu | Ser | Leu 380 | Gly | Lys |

( 2 ) INFORMATION FOR SEQ ID NO: 8:

( i ) SEQUENCE CHARACTERISTICS:
( A ) LENGTH: 984 base pairs
( B ) TYPE: nucleic acid
( C ) STRANDEDNESS: double
( D ) TOPOLOGY: linear ( x i ) SEQUENCE DESCRIPTION: SEQ ID NO: 8:

```
GCTAGTACCA AGGGCCCATC CGTCTTCCCC CTGGCGCCCT GCTCCAGGAG CACCTCCGAG        60
AGCACGGCCG CCCTGGGCTG CCTGGTCAAG GACTACTTCC CCGAACCGGT GACGGTGTCG       120
TGGAACTCAG GCGCCCTGAC CAGCGGCGTG CACACCTTCC CGGCTGTCCT ACAGTCCTCA       180
GGACTCTACT CCCTCAGCAG CGTGGTGACC GTGCCCTCCA GCAGCTTGGG CACGAAGACC       240
TACACCTGCA ACGTAGATCA CAAGCCCAGC AACACCAAGG TGGACAAGAG AGTTGAGTCC       300
AAATATGGTC CCCCATGCCC ACCATGCCCA GCGCCTGAAT TTGAGGGGGG ACCATCAGTC       360
TTCCTGTTCC CCCCAAAACC CAAGGACACT CTCATGATCT CCCGGACCCC TGAGGTCACG       420
TGCGTGGTGG TGGACGTGAG CCAGGAAGAC CCCGAGGTCC AGTTCAACTG GTACGTGGAT       480
GGCGTGGAGG TGCATAATGC CAAGACAAAG CCGCGGGAGG AGCAGTTCAA CAGCACGTAC       540
CGTGTGGTCA GCGTCCTCAC CGTCCTGCAC CAGGACTGGC TGAACGGCAA GGAGTACAAG       600
TGCAAGGTCT CCAACAAAGG CCTCCCGTCA TCGATCGAGA AAACCATCTC CAAAGCCAAA       660
GGGCAGCCCC GAGAGCCACA GGTGTACACC CTGCCCCCAT CCCAGGAGGA GATGACCAAG       720
AACCAGGTCA GCCTGACCTG CCTGGTCAAA GGCTTCTACC CCAGCGACAT CGCCGTGGAG       780
TGGGAGAGCA ATGGGCAGCC GGAGAACAAC TACAAGACCA CGCCTCCCGT GCTGGACTCC       840
GACGGATCCT TCTTCCTCTA CAGCAGGCTA ACCGTGGACA AGAGCAGGTG GCAGGAGGGG       900
AATGTCTTCT CATGCTCCGT GATGCATGAG GCTCTGCACA ACCACTACAC ACAGAAGAGC       960
CTCTCCCTGT CTCTGGGTAA ATGA                                             984
```

( 2 ) INFORMATION FOR SEQ ID NO: 9:

( i ) SEQUENCE CHARACTERISTICS:
    ( A ) LENGTH: 1149 base pairs
    ( B ) TYPE: nucleic acid
    ( C ) STRANDEDNESS: double
    ( D ) TOPOLOGY: linear ( x i ) SEQUENCE DESCRIPTION: SEQ ID NO: 9:

| | | | | | |
|---|---|---|---|---|---|
| ATGGGTCTCA | CCTCCCAACT | GCTTCCCCCT | CTGTTCTTCC | TGCTAGCATG | TGCCGGCAAC | 60 |
| TTTGTCCACG | GACACAAGTG | CGATATCACC | TTACAGGAGA | TCATCAAAAC | TTTGAACAGC | 120 |
| CTCACAGAGC | AGAAGACTCT | GTGCACCGAG | TTGACCGTAA | CAGACATCTT | TGCTGCCTCC | 180 |
| AAGAACACAA | CTGAGAAGGA | AACCTTCTGC | AGGGCTGCGA | CTGTGCTCCG | GCAGTTCTAC | 240 |
| AGCCACCATG | AGAAGGACAC | TCGCTGCCTG | GGTGCGACTG | CACAGCAGTT | CCACAGGCAC | 300 |
| AAGCAGCTGA | TCCGATTCCT | GAAACGGCTC | GACAGGAACC | TCTGGGGCCT | GGCGGGCTTG | 360 |
| AATTCCTGTC | CTGTGAAGGA | AGCCAACCAG | AGTACGTTGG | AAAACTTCTT | GGAAAGGCTA | 420 |
| AAGACGATCA | TGAGAGAGAA | AGACTCAAAG | TGCTCGAGCG | AGTCCAAATA | TGGTCCCCCA | 480 |
| TGCCCACCAT | GCCCAGCGCC | TGAATTTGAG | GGGGACCAT  | CAGTCTTCCT | GTTCCCCCCA | 540 |
| AAACCCAAGG | ACACTCTCAT | GATCTCCCGG | ACCCCTGAGG | TCACGTGCGT | GGTGGTGGAC | 600 |
| GTGAGCCAGG | AAGACCCCGA | GGTCCAGTTC | AACTGGTACG | TGGATGGCGT | GGAGGTGCAT | 660 |
| AATGCCAAGA | CAAAGCCGCG | GGAGGAGCAG | TTCAACAGCA | CGTACCGTGT | GGTCAGCGTC | 720 |
| CTCACCGTCC | TGCACCAGGA | CTGGCTGAAC | GGCAAGGAGT | ACAAGTGCAA | GGTCTCCAAC | 780 |
| AAAGGCCTCC | CGTCATCGAT | CGAGAAAACC | ATCTCCAAAG | CCAAAGGGCA | GCCCCGAGAG | 840 |
| CCACAGGTGT | ACACCCTGCC | CCCATCCCAG | GAGGAGATGA | CCAAGAACCA | GGTCAGCCTG | 900 |
| ACCTGCCTGG | TCAAAGGCTT | CTACCCCAGC | GACATCGCCG | TGGAGTGGGA | GAGCAATGGG | 960 |
| CAGCCGGAGA | ACAACTACAA | GACCACGCCT | CCCGTGCTGG | ACTCCGACGG | ATCCTTCTTC | 1020 |
| CTCTACAGCA | GGCTAACCGT | GGACAAGAGC | AGGTGGCAGG | AGGGGAATGT | CTTCTCATGC | 1080 |
| TCCGTGATGC | ATGAGGCTCT | GCACAACCAC | TACACACAGA | AGAGCCTCTC | CCTGTCTCTG | 1140 |
| GGTAAATGA  | | | | | | 1149 |

( 2 ) INFORMATION FOR SEQ ID NO: 10:

( i ) SEQUENCE CHARACTERISTICS:
    ( A ) LENGTH: 382 amino acids
    ( B ) TYPE: amino acid
    ( C ) STRANDEDNESS:
    ( D ) TOPOLOGY: linear ( x i ) SEQUENCE DESCRIPTION: SEQ ID NO: 10:

| Met | Gly | Leu | Thr | Ser | Gln | Leu | Leu | Pro | Pro | Leu | Phe | Phe | Leu | Leu | Ala |
|---|---|---|---|---|---|---|---|---|---|---|---|---|---|---|---|
| 1 | | | | 5 | | | | | 10 | | | | | 15 | |
| Cys | Ala | Gly | Asn | Phe | Val | His | Gly | His | Lys | Cys | Asp | Ile | Thr | Leu | Gln |
| | | | 20 | | | | 25 | | | | | 30 | | | |
| Glu | Ile | Ile | Lys | Thr | Leu | Asn | Ser | Leu | Thr | Glu | Gln | Lys | Thr | Leu | Cys |
| | | 35 | | | | | 40 | | | | | 45 | | | |
| Thr | Glu | Leu | Thr | Val | Thr | Asp | Ile | Phe | Ala | Ala | Ser | Lys | Asn | Thr | Thr |
| | 50 | | | | | 55 | | | | | 60 | | | | |
| Glu | Lys | Glu | Thr | Phe | Cys | Arg | Ala | Ala | Thr | Val | Leu | Arg | Gln | Phe | Tyr |
| 65 | | | | | 70 | | | | | 75 | | | | | 80 |
| Ser | His | His | Glu | Lys | Asp | Thr | Arg | Cys | Leu | Gly | Ala | Thr | Ala | Gln | Gln |
| | | | | 85 | | | | | 90 | | | | | 95 | |
| Phe | His | Arg | His | Lys | Gln | Leu | Ile | Arg | Phe | Leu | Lys | Arg | Leu | Asp | Arg |
| | | | | 100 | | | | | 105 | | | | | 110 | |

|          |     |     |     |     |     |     |     |     |     |     |     |     |     |     |     |
|----------|-----|-----|-----|-----|-----|-----|-----|-----|-----|-----|-----|-----|-----|-----|-----|
| Asn | Leu | Trp<br>115 | Gly | Leu | Ala | Gly<br>120 | Leu | Asn | Ser | Cys | Pro<br>125 | Val | Lys | Glu | Ala |
| Asn | Gln<br>130 | Ser | Thr | Leu | Glu | Asn<br>135 | Phe | Leu | Glu | Arg | Leu<br>140 | Lys | Thr | Ile | Met |
| Arg<br>145 | Glu | Lys | Asp | Ser | Lys<br>150 | Cys | Ser | Ser | Glu | Ser<br>155 | Lys | Tyr | Gly | Pro | Pro<br>160 |
| Cys | Pro | Pro | Cys | Pro<br>165 | Ala | Pro | Glu | Phe | Glu<br>170 | Gly | Gly | Pro | Ser | Val<br>175 | Phe |
| Leu | Phe | Pro | Pro<br>180 | Lys | Pro | Lys | Asp | Thr<br>185 | Leu | Met | Ile | Ser | Arg<br>190 | Thr | Pro |
| Glu | Val | Thr<br>195 | Cys | Val | Val | Val | Asp<br>200 | Val | Ser | Gln | Glu | Asp<br>205 | Pro | Glu | Val |
| Gln | Phe | Asn<br>210 | Trp | Tyr | Val | Asp<br>215 | Gly | Val | Glu | Val | His<br>220 | Asn | Ala | Lys | Thr |
| Lys<br>225 | Pro | Arg | Glu | Glu | Gln<br>230 | Phe | Asn | Ser | Thr | Tyr<br>235 | Arg | Val | Val | Ser | Val<br>240 |
| Leu | Thr | Val | Leu | His<br>245 | Gln | Asp | Trp | Leu | Asn<br>250 | Gly | Lys | Glu | Tyr | Lys<br>255 | Cys |
| Lys | Val | Ser | Asn<br>260 | Lys | Gly | Leu | Pro | Ser<br>265 | Ser | Ile | Glu | Lys | Thr<br>270 | Ile | Ser |
| Lys | Ala | Lys<br>275 | Gly | Gln | Pro | Arg | Glu<br>280 | Pro | Gln | Val | Tyr | Thr<br>285 | Leu | Pro | Pro |
| Ser | Gln<br>290 | Glu | Glu | Met | Thr | Lys<br>295 | Asn | Gln | Val | Ser | Leu<br>300 | Thr | Cys | Leu | Val |
| Lys<br>305 | Gly | Phe | Tyr | Pro | Ser<br>310 | Asp | Ile | Ala | Val | Glu<br>315 | Trp | Glu | Ser | Asn | Gly<br>320 |
| Gln | Pro | Glu | Asn | Asn<br>325 | Tyr | Lys | Thr | Thr | Pro<br>330 | Pro | Val | Leu | Asp | Ser<br>335 | Asp |
| Gly | Ser | Phe | Phe<br>340 | Leu | Tyr | Ser | Arg | Leu<br>345 | Thr | Val | Asp | Lys | Ser<br>350 | Arg | Trp |
| Gln | Glu | Gly<br>355 | Asn | Val | Phe | Ser | Cys<br>360 | Ser | Val | Met | His | Glu<br>365 | Ala | Leu | His |
| Asn | His | Tyr<br>370 | Thr | Gln | Lys | Ser<br>375 | Leu | Ser | Leu | Ser | Leu<br>380 | Gly | Lys |     |     |

( 2 ) INFORMATION FOR SEQ ID NO: 11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

```
CGAACCACTG AATTCCGCAT TGCAGAGATA                                      30
```

( 2 ) INFORMATION FOR SEQ ID NO: 12:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

```
CACAAAGATC CTTAGGTACC GCTCGAACAC TTTGA                                35
```

( 2 ) INFORMATION FOR SEQ ID NO: 13:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 13:

TCGAGCTCGG TACCGAGCCC AAATCGGCCG ACAAAACTCA CAC    43

( 2 ) INFORMATION FOR SEQ ID NO: 14:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 14:

GTACTGCTCC TCCCGCGGCT TTGTCTTG    28

( 2 ) INFORMATION FOR SEQ ID NO: 15:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 15:

AATTCGGTTA CCTGCAGATA TCAAGCT    27

( 2 ) INFORMATION FOR SEQ ID NO: 16:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 16:

AATTAGCTTG ATATCTGCAG GTAACCG    27

( 2 ) INFORMATION FOR SEQ ID NO: 17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 17:

CACAAGTGCG ATATCACCTT ACAGGAGATC    30

( 2 ) INFORMATION FOR SEQ ID NO: 18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 18:

CTCGGTACCG CTCGAGCACT TTGAGTCTTT    30

( 2 ) INFORMATION FOR SEQ ID NO: 19:

( i ) SEQUENCE CHARACTERISTICS:
        ( A ) LENGTH: 30 base pairs (B) TYPE: nucleic acid
(C) STRANDEDNESS: single
(D) TOPOLOGY: linear (xi) SEQUENCE DESCRIPTION: SEQ ID NO: 19:

GGTGGACAAC TCGAGCGAGT CCAAATATGG    30

(2) INFORMATION FOR SEQ ID NO: 20:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (xi) SEQUENCE DESCRIPTION: SEQ ID NO: 20:

TTACGTAGAT CTAGACTACA CTCATTTACC    30

(2) INFORMATION FOR SEQ ID NO: 21:

(i) SEQUENCE CHARACTERISTICS:
  (A) LENGTH: 129 amino acids
  (B) TYPE: amino acid
  (C) STRANDEDNESS: Not Relevant
  (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:21:

| His | Lys | Cys | Asp | Ile | Thr | Leu | Gln | Glu | Ile | Ile | Lys | Thr | Leu | Asn | Ser |
| 1 | | | | 5 | | | | | 10 | | | | | 15 | |
| Leu | Thr | Glu | Gln | Lys | Thr | Leu | Cys | Thr | Glu | Leu | Thr | Val | Thr | Asp | Ile |
| | | | 20 | | | | 25 | | | | | | 30 | | |
| Phe | Ala | Ala | Ser | Lys | Asn | Thr | Thr | Glu | Lys | Glu | Thr | Phe | Cys | Arg | Ala |
| | | 35 | | | | | 40 | | | | | 45 | | | |
| Ala | Thr | Val | Leu | Arg | Gln | Phe | Tyr | Ser | His | His | Glu | Lys | Asp | Thr | Arg |
| | 50 | | | | | 55 | | | | | 60 | | | | |
| Cys | Leu | Gly | Ala | Thr | Ala | Gln | Gln | Phe | His | Arg | His | Lys | Gln | Leu | Ile |
| 65 | | | | | 70 | | | | | 75 | | | | | 80 |
| Arg | Phe | Leu | Lys | Arg | Leu | Asp | Arg | Asn | Leu | Trp | Gly | Leu | Ala | Gly | Leu |
| | | | | 85 | | | | | 90 | | | | | 95 | |
| Asn | Ser | Cys | Pro | Val | Lys | Glu | Ala | Asn | Gln | Ser | Thr | Leu | Glu | Asn | Phe |
| | | | 100 | | | | | 105 | | | | | 110 | | |
| Leu | Glu | Arg | Leu | Lys | Thr | Ile | Met | Arg | Glu | Lys | Tyr | Ser | Lys | Cys | Ser |
| | | 115 | | | | | 120 | | | | | 125 | | | |
| Ser | | | | | | | | | | | | | | | |

THERAPEUTIC USES OF FUSION PROTEINS BETWEEN MUTANT IL 4/IL13 ANTAGONISTS AND IMMUNOGLOBULINS

The present invention relates to antagonists of human interleukin 4 (IL4) and/or human interleukin 13 (IL13) for the treatment of conditions resulting from undesirable actions of IL4 and/or IL13 such as certain IgE mediated allergic diseases, T cell mediated autoimmune conditions and inappropriate immune responses to infectious agents.

Interleukins are secreted peptide mediators of the immune response. Each of the known interleukins has many effects on the development, activation, proliferation and differentiation of cells of the immune system. IL4 has a physiological role in such functions, but can also contribute to the pathogenesis of disease. In particular IL4 is associated with the pathway of B lymphocyte development that leads to the generation of IgE antibodies that are the hallmark of allergic diseases such as extrinsic asthma, rhinitis, allergic conjunctivitis, atopic dermatitis and anaphylaxis. IL4 can also act as a general growth and differentiation factor for T lymphocytes that may contribute to tissue damage in certain autoimmune conditions such as insulin dependent diabetes, multiple sclerosis and rheumatoid arthritis and in graft rejection. IL4 can also suppress the generation of cell-mediated responses required for the control of infectious disease. Antagonism of the effect of IL4 on T or B lymphocytes can therefore be expected to have beneficial effects on such diseases. IL13 has been recently identified and shares similarity in many of the biological properties of IL4 (Minty, A. et al (1993), Nature 362, 248–250) including some aspect(s) of receptor structure/function (Aversa, G. et al (1993), J. Exp. Med. 178, 2213–2218).

Human IL4 consists of a single polypeptide chain of 129 amino acids with 2 possible N-glycosylation sites and 6 cysteines involved in 3 disulphide bridges (Le, H. V. et. al., (1988), J. Biol. Chem. 263, 10817–10823). The amino acid sequence of IL4 and the positions of these disulphide bridges are known (Carr, C. et al., (1991) Biochemistry 30, 1515–1523) SEQ ID NO:21.

varies with the extent of glycosylation from 15 KDa (no glycosylation) to 60 KDa or more (hyperglycosylated IL4).

The DNA sequence for human IL4 has also been described by Yokota, T. et. al., P.N.A.S. 1986 83 5894–5898.

WO 93/10235 describes certain mutants of IL4 which are IL4 antagonists or partial antagonists.

EP-A-0 464 533 discloses fusion proteins comprising various portions of the constant region of immunoglobulin molecules together with another human protein or part thereof.

The present invention provides a soluble protein having IL4 and/or IL13 antagonist or partial antagonist activity, comprising an IL4 mutant or variant fused to least one human immunoglobulin constant domain or fragment thereof.

The term "mutant or variant" encompasses any molecule such as a truncated or other derivative of the IL4 protein which retains the ability to antagonise IL4 and/or IL13 following internal administration to a human. Such other derivatives can be prepared by the addition, deletion, substitution, or rearrangement of amino acids or by chemical modifications thereof.

DNA polymers which encode mutants or variants of IL4 may be prepared by site-directed mutagenesis of the cDNA which codes for IL4 by conventional methods such as those described by G. Winter et al in Nature 1982, 299, 756–758 or by Zoller and Smith 1982; Nucl. Acids Res., 10, 6487–6500, or deletion mutagenesis such as described by Chan and Smith in Nucl. Acids Res., 1984, 12, 2407–2419 or by G. Winter et al in Biochem. Soc. Trans., 1984; 12, 224–225 or polymerase chain reaction such as described by Mikaelian and Sergeant in Nucleic Acids Research, 1992, 20, 376.

As used herein, "having IL4 and/or IL13 antagonist or partial antagonist activity" means that, in the assay described by Spits et al (J. Immunology 139, 1142 (1987)), IL4-stimulated T cell proliferation is inhibited in a dose-dependent manner.

Suitable IL4 mutants are disclosed in WO 93/10235, wherein at least one amino acid, naturally occurring in wild type IL4 at any one of positions 120 to 128 inclusive, is

```
                                    10
HIS—LYS—CYS—ASP—ILE—THR—LEU—GLN—GLU—ILE—ILE—LYS—THR—LEU—ASN—

20                                          30
SER—LEU—THR—GLU—GLN—LYS—THR—LEU—CYS—THR—GLU—LEU—THR—VAL—THR—

40
ASP—ILE—PHE—ALA—ALA—SER—LYS—ASN—THR—THR—GLU—LYS—GLU—THR—PHE—

50                                          60
CYS—ARG—ALA—ALA—THR—VAL—LEU—ARG—GLN—PHE—TYR—SER—HIS—HIS—GLU—

70
LYS—ASP—THR—ARG—CYS—LEU—GLY—ALA—THR—ALA—GLN—GLN—PHE—HIS—ARG—

80                                          90
HIS—LYS—GLN—LEU—ILE—ARG—PHE—LEU—LYS—ARG—LEU—ASP—ARG—ASN—LEU—

100
TRP—GLY—LEU—ALA—GLY—LEU—ASN—SER—CYS—PRO—VAL—LYS—GLU—ALA—ASN—

110                                         120
GLN—SER—THR—LEU—GLU—ASN—PHE—LEU—GLU—ARG—LEU—LYS—THR—ILE—MET—

129
ARG—GLU—LYS—TYR—SER—LYS—CYS—SER—SER
```

The disulphide bridges are between residues 3 and 127, 24 and 65, and 46 and 99. The molecular weight of IL4 replaced by a different natural amino acid. In particular, the tyrosine naturally occurring at position 124 may be replaced by a different natural amino acid, such as glycine or, more preferably, aspartic acid.

The immunoglobulin may be of any subclass (IgG, IgM, IgA, IgE), but is preferably IgG, such as IgG1, IgG3 or IgG4. The said constant domain(s) or fragment thereof may be derived from the heavy or light chain or both. The invention encompasses mutations in the immunoglobulin component which eliminate undesirable properties of the native immunoglobulin, such as Fc receptor binding and/or introduce desirable properties such as stability. For example, Angal S., King D. J., Bodmer M. W., Turner A., Lawson A. D. G., Roberts G., Pedley B. and Adair R., Molecular Immunology vol30pp105–108, 1993, describe an IgG4 molecule where residue 241 (Kabat numbering) is altered from serine to proline. This change increases the serum half-life of the IgG4 molecule. Canfield S. M. and Morrison S. L., Journal of Experimental Medicine vol173pp1483–1491, describe the alteration of residue 248 (Kabat numbering) from leucine to glutamate in IgG3 and from glutamate to leucine in mouse IgG2b. Substitution of leucine for glutamate in the former decreases the affinity of the immunoglobulin molecule concerned for the FcγRI receptor, and substitution of glutamate for leucine in the latter increases the affinity. EP0307434 discloses various mutations including an L to E mutation at residue 248 (Kabat numbering) in IgG.

The constant domain(s) or fragment thereof is preferably the whole or a substantial part of the constant region of the heavy chain of human IgG, most preferably IgG4. In one aspect the IgG component consists of the CH2 and CH3 domains and the hinge region of IgG1 including cysteine residues contributing to inter-heavy chain disulphide bonding, for example residues 11 and 14 of the IgG1 hinge region (Frangione B. and Milstein C., Nature vol216pp939–941, 1967). Preferably the IgG1 component consists of amino acids corresponding to residues 1-4 and 6-15 of the hinge, 1-110 of CH2 and 1-107 of CH3 of IgG1 described by Ellison J., Berson B. and Hood L. E., Nucleic Acids Research vol10, pp4071–4079, 1982. Residue 5 of the hinge is changed from cysteine in the published IgG1 sequence to alanine by alteration of TGT to GCC in the nucleotide sequence. In another aspect the IgG component is derived from IgG4, comprising the CH2 and CH3 domains and the hinge region including cysteine residues contributing to inter-heavy chain disulphide bonding, for example residues 8 and 11 of the IgG4 hinge region (Pinck J. R. and Milstein C., Nature vol216pp941–942, 1967). Preferably the IgG4 component consists of amino acids corresponding to residues 1–12 of the hinge, 1-110 of CH2 and 1-107 of CH3 of IgG4 described by Ellison J., Buxbaum J. and Hood L., DNA vol1pp11–18, 1981. In one example of a suitable mutation in IgG4, residue 10 of the hinge (residue 241, Kabat numbering) is altered from serine (S) in the wild type to proline (P) and residue 5 of CH2 (residue 248, Kabat numbering) is altered from leucine (L) in the wild type to glutamate (E).

Fusion of the IL4 mutant or variant to the Ig constant domain or fragment is by C-terminus of one component to N-terminus of the other. Preferably the IL4 mutant or variant is fused via its C-terminus to the N-terminus of the Ig constant domain or fragment.

In a preferred aspect, the amino acid sequence of the fusion protein of the invention is represented by SEQ ID No:4, SEQ ID No:7 or SEQ ID No:10.

In a further aspect, the invention provides a process for preparing a compound according to the invention which process comprises expressing DNA encoding said compound in a recombinant host cell and recovering the product.

The DNA polymer comprising a nucleotide sequence that encodes the compound also forms part of the invention.

In a preferred aspect the DNA polymer comprises or consists of the sequence of SEQ ID No:3, SEQ ID No:6 or SEQ ID No:9.

The process of the invention may be performed by conventional recombinant techniques such as described in Maniatis et. al., Molecular Cloning—A Laboratory Manual; Cold Spring Harbor, 1982 and DNA Cloning vols I, II and III (D. M. Glover ed., IRL Press Ltd).

In particular, the process may comprise the steps of:

i) preparing a replicable expression vector capable, in a host cell, of expressing a DNA polymer comprising a nucleotide sequence that encodes said compound;
ii) transforming a host cell with said vector;
iii) culturing said transformed host cell under conditions permitting expression of said DNA polymer to produce said compound; and
iv) recovering said compound.

The invention also provides a process for preparing the DNA polymer by the condensation of appropriate mono-, di- or oligomeric nucleotide units.

The preparation may be carried out chemically, enzymatically, or by a combination of the two methods, in vitro or in vivo as appropriate. Thus, the DNA polymer may be prepared by the enzymatic ligation of appropriate DNA fragments, by conventional methods such as those described by D. M. Roberts et al in Biochemistry 1985, 24, 5090–5098.

The DNA fragments may be obtained by digestion of DNA containing the required sequences of nucleotides with appropriate restriction enzymes, by chemical synthesis, by enzymatic polymerisation on DNA or RNA templates, or by a combination of these methods.

Digestion with restriction enzymes may be performed in an appropriate buffer at a temperature of 20°–70° C., generally in a volume of 50 μl or less with 0.1–10 μg DNA.

Enzymatic polymerisation of DNA may be carried out in vitro using a DNA polymerase such as DNA polymerase I (Klenow fragment) in an appropriate buffer containing the nucleoside triphosphates dATP, dCTP, dGTP and dTTP as required at a temperature of 10°–37° C., generally in a volume of 50 μl or less.

Enzymatic ligation of DNA fragments may be carried out using a DNA ligase such as T4 DNA ligase in an appropriate buffer at a temperature of 4° C. to ambient, generally in a volume of 50 μl or less.

The chemical synthesis of the DNA polymer or fragments may be carried out by conventional phosphotriester, phosphite or phosphoramidite chemistry, using solid phase techniques such as those described in 'Chemical and Enzymatic Synthesis of Gene Fragments—A Laboratory Manual' (ed. H. G. Gassen and A. Lang), Verlag Chemie, Weinheim (1982),or in other scientific publications, for example M. J. Gait, H. W. D. Matthes, M. Singh, B. S. Sproat, and R. C. Titmas, Nucleic Acids Research, 1982, 10, 6243; B. S. Sproat and W. Bannwarth, Tetrahedron Letters, 1983, 24, 5771; M. D. Matteucci and M. H Caruthers, Tetrahedron Letters, 1980, 21, 719; M. D. Matteucci and M. H. Caruthers, Journal of the American Chemical Society, 1981, 103, 3185; S. P. Adams et al., Journal of the American Chemical Society,1983, 105, 661; N. D. Sinha, J. Biernat, J. McMannus, and H. Koester, Nucleic Acids Research, 1984, 12, 4539; and H. W. D. Matthes et al., EMBO Journal, 1984, 3, 801. Preferably an automated DNA synthesizer is employed.

The DNA polymer is preferably prepared by ligating two or more DNA molecules which together comprise a DNA sequence encoding the compound. A particular process in accordance with the invention comprises ligating a first DNA molecule encoding a said IL4 mutant or variant and a second DNA molecule encoding a said immunoglobulin domain or fragment thereof.

The DNA molecules may be obtained by the digestion with suitable restriction enzymes of vectors carrying the required coding sequences or by use of polymerase chain reaction technology.

The precise structure of the DNA molecules and the way in which they are obtained depends upon the structure of the desired product. The design of a suitable strategy for the construction of the DNA molecule coding for the compound is a routine matter for the skilled worker in the art.

The expression of the DNA polymer encoding the compound in a recombinant host cell may be carried out by means of a replicable expression vector capable, in the host cell, of expressing the DNA polymer. The expression vector is novel and also forms part of the invention.

The replicable expression vector may be prepared in accordance with the invention, by cleaving a vector compatible with the host cell to provide a linear DNA segment having an intact replicon, and combining said linear segment with one or more DNA molecules which, together with said linear segment, encode the compound, under ligating conditions.

The ligation of the linear segment and more than one DNA molecule may be carried out simultaneously or sequentially as desired.

Thus, the DNA polymer may be preformed or formed during the construction of the vector, as desired.

The choice of vector will be determined in part by the host cell, which may be prokaryotic, such as *E. coli*, or eukaryotic, such as mouse C127, mouse myeloma, chinese hamster ovary or Hela cells, fungi e.g. filamentous fungi or unicellular yeast or an insect cell such as Drosophila. The host cell may also be a transgenic animal. Suitable vectors include plasmids, bacteriophages, cosmids and recombinant viruses derived from, for example, baculoviruses, vaccinia or Semliki Forest virus.

The preparation of the replicable expression vector may be carried out conventionally with appropriate enzymes for restriction, polymerisation and ligation of the DNA, by procedures described in, for example, Maniatis et al., cited above. Polymerisation and ligation may be performed as described above for the preparation of the DNA polymer. Digestion with restriction enzymes may be performed in an appropriate buffer at a temperature of 20°–70° C., generally in a volume of 50 μl or less with 0.1–10 μg DNA.

The recombinant host cell is prepared, in accordance with the invention, by transforming a host cell with a replicable expression vector of the invention under transforming conditions. Suitable transforming conditions are conventional and are described in, for example, Maniatis et al., cited above, or "DNA Cloning" Vol. II, D. M. Glover ed., IRL Press Ltd, 1985.

The choice of transforming conditions is determined by the host cell. Thus, a bacterial host such as *E. coli* may be treated with a solution of $CaCl_2$ (Cohen et al, Proc. Nat. Acad. Sci., 1973, 69, 2110) or with a solution comprising a mixture of RbCl, $MnCl_2$, potassium acetate and glycerol, and then with 3-[N-morpholino]propane-sulphonic acid, RbCl and glycerol. Mammalian cells in culture may be transformed by calcium co-precipitation of the vector DNA onto the cells.

The invention also extends to a host cell transformed with a replicable expression vector of the invention.

Culturing the transformed host cell under conditions permitting expression of the DNA polymer is carried out conventionally, as described in, for example, Maniatis et al and "DNA Cloning" cited above. Thus, preferably the cell is supplied with nutrient and cultured at a temperature below 45° C.

The expression product is recovered by conventional methods according to the host cell. Thus, where the host cell is bacterial, such as *E. coli* it may be lysed physically, chemically or enzymatically and the protein product isolated from the resulting lysate. If the product is to be secreted from the bacterial cell it may be recovered from the periplasmic space or the nutrient medium. Where the host cell is mammalian, the product may generally be isolated from the nutrient medium.

The DNA polymer may be assembled into vectors designed for isolation of stable transformed mammalian cell lines expressing the product; e.g. bovine papillomavirus vectors or amplified vectors in chinese hamster ovary cells (DNA cloning Vol.11 D. M. Glover ed. IRL Press 1985; Kaufman, R. J. et al., Molecular and Cellular Biology 5, 1750–1759, 1985; Pavlakis G. N. and Hamer, D. H., Proceedings of the National Academy of Sciences (USA) 80, 397–401, 1983; Goeddel, D. V. et al., European Patent Application No. 0093619, 1983).

Compounds of the present invention have IL4 and/or IL13 antagonist activity and are therefore of potential use in the treatment of conditions resulting from undesirable actions of IL4 and/or IL13 such as IgE mediated allergic diseases and T cell mediated autoimmune conditions or chronic microbial infection.

The invention therefore further provides a pharmaceutical composition comprising a compound of the invention and a pharmaceutically acceptable carrier.

In use the compound will normally be employed in the form of a pharmaceutical composition in association with a human pharmaceutical carrier, diluent and/or excipient, although the exact form of the composition will depend on the mode of administration. The compound may, for example, be employed in the form of aerosol or nebulisable solution for inhalation or sterile solutions for parenteral administration.

The dosage ranges for administration of the compounds of the present invention are those to produce the desired effect on the IL4 and/or IL13 mediated condition, for example whereby IgE antibody mediated symptoms are reduced or progression of the autoimmune disease is halted or reversed. The dosage will generally vary with age, extent or severity of the medical condition and contraindications, if any. The unit dosage can vary from less than 1 mg to 300 mg, but typically will be in the region of 1 to 20 mg per dose, in one or more doses, such as one to six doses per day, such that the daily dosage is in the range 0.02–40 mg/kg.

Compositions suitable for injection may be in the form of solutions, suspensions or emulsions, or dry powders which are dissolved or suspended in a suitable vehicle prior to use.

Fluid unit dosage forms are prepared utilising the compound and a pyrogen-free sterile vehicle. The compound, depending on the vehicle and concentration used, can be either dissolved or suspended in the vehicle. Solutions may be used for all forms of parenteral administration, and are particularly used for intravenous infection. In preparing solutions the compound can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and/or local anaesthetic agents may be dissolved in the vehicle.

Dry powders which are dissolved or suspended in a suitable vehicle prior to use may be prepared by filling pre-sterilised drug substance and other ingredients into a sterile container using aseptic technique in a sterile area. Alternatively the drug and other ingredients may be dissolved in an aqueous vehicle, the solution is sterilised by filtration and distributed into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile compound is suspended in the sterile vehicle, instead of being dissolved and sterilisation cannot be accomplished by filtration. The compound may be isolated in a sterile state or alternatively it may be sterilised after isolation, e.g. by gamma irradiation. Advantageously, a suspending agent for example polyvinylpyrrolidone is included in the composition to facilitate uniform distribution of the compound.

Compositions suitable for administration via the respiratory tract include aerosols, nebulisable solutions or microfine powders for insufflation. In the latter case, particle size of less than 50 microns, especially less than 10 microns, is preferred. Such compositions may be made up in a conventional manner and employed in conjunction with conventional administration devices.

In a further aspect there is provided a method of treating conditions resulting from undesirable actions of IL4 and/or IL13 which comprises administering to the sufferer an effective amount of a compound of the invention.

The invention further provides a compound of the invention for use as an active therapeutic substance, in particular for use in treating conditions resulting from undesirable actions of IL4 and/or IL13.

The invention also provides the use of a compound of the invention in the manufacture of a medicament for treating conditions resulting from undesirable actions of IL4 and/or IL13.

No unexpected toxicological effects are expected when compounds of the invention are administered in accordance with the present invention.

The following Examples illustrate the invention.

EXAMPLE 1
IL4.Y124D/IgG1 fusion protein

The construction of an IL4.Y124D/IgG1 chimeric cDNA, the expression of the corresponding protein in a mammalian expression system and its activity are described.

1. Construction of DNA coding for fusion protein
(a) Construction of IL4.Y124D coding region A variant of the human IL4 gene, which has been described (Kruse, N, Tony, H-P and Sebald, W. EMBO Journal 11: 3237 [1992]) in which residue 124 in the protein has been mutated from tyrosine in the wild type to aspartic acid, was produced by PCR mutagenesis of the human IL4 cDNA (purchased from British Biotechnology). The IL4.Y124D cDNA was inserted into the expression vector pTR312, using the HindIII and BglII sites, (M. J. Browne, J. E. Carey, C. G. Chapman, A. W. R. Tyrrell, C. Entwisle, G. M. P. Lawrence, B. Reavy, I. Dodd, A. Esmail & J. H. Robinson. Journal of Biological Chemistry 263: 1599, [1988]) to form the plasmid pDB906.

To amplify the IL4.Y124D molecule and add convenient restriction sites at each end for subcloning, a PCR reaction was performed using 20 ng of the pDB906 plasmid as the substrate. PCR primers were designed to include restriction enzyme sites, flanked by 10–15 nucleotide base pairs to "anchor" the primers at each end. The primer sequences were as follows:

1) 5' CGA ACC ACT GAA TTC CGC ATT GCA GAG ATA 3' (SEQ ID NO:11)

(includes an EcoRI restriction site, GAATTC)

2) 5' CAC AAA GAT CCT TAG GTA CCG CTC GAA CAC TTT GA 3' (SEQ ID NO:12)

(includes a KpnI restriction site, GGTACC)

Primers were used at a final concentration of 5 ng/μl, and dNTPs were added at a final concentration of 0.2 mM in a total reaction volume of 100 μl. 31 cycles of PCR were performed. Cycles consisted of a denaturation step of 1 minute at 94° C., an annealing step of 1 minute 30 seconds at 50° C., and an elongation step of 1 minute 30 seconds at 72° C. On cycle 1 denaturation was extended to 5 minutes and on the final cycle elongation was extended to 7 minutes. 2.5 units of the Taq polymerase enzyme from Advanced Biotechnologies were used in the PCR reaction. A PCR product of 587 bp was produced. This was purified using the Promega "Magic PCR cleanup" kit, and then digested with EcoRI and KpnI in react buffer 4 (all restriction enzymes were obtained from GibcoBRL.), to generate 'sticky ends'. After 4 hours 30 minutes at 37° C., the reaction was heated to 70° C. for 10 minutes and then ethanol precipitated. Analysis of the resulting DNA by agarose gel electrophoresis showed the presence of three bands of approximately 570 bp, 463 bp and 100 bp. The 570 bp fragment represents the full-length IL4.Y124D variant of IL4 and was present because the digest was incomplete. The two smaller fragments were produced due to the presence of an EcoRI site within the IL4.Y124D cDNA. The 570 bp band was purified by the Geneclean™ procedure, and ligated into Bluescript KS+™ which was prepared by digestion with EcoRI and KpnI followed by Geneclean™. A Bluescript KS+/IL4.Y124D recombinant was thus generated. Large amounts of this recombinant DNA were produced using the Promega "Magic Maxiprep" method. The IL4.Y124D insert was excised from the Bluescript recombinant using SmaI and KpnI. 20 μg recombinant DNA was incubated with 25 units SmaI in react buffer 4, at 30° C. overnight. 25 units of KpnI were then added to the digest, which was incubated at 37° C. for 5 hours. The resulting fragment of approximately 580 bp was purified by Geneclean TM to generate an IL4.Y124D/SmaI/KpnI fragment.

(b) Construction of IgG1 coding region

The COSFcLink vector (Table 1) contains human IgG1 cDNA encoding amino acids 1-4 and 6-15 of the hinge, 1-110 of CH2 and 1-108 of CH3 described by Ellison J., Berson B. and Hood L. E., Nucleic Acids Research vol10, pp4071–4079, 1982. Residue 5 of the hinge is changed from cysteine in the published IgG1 sequence to alanine by alteration of TGT to GCC in the nucleotide sequence. This was cloned from the human IgG plasma cell leukemia ARH-77 (American Type Tissue Collection), using RT-PCR and fully sequenced to confirm identity with the publish ed sequence [patent application publication WO 92/00985].

The construction of COSFc began with a pUC 18 vector containing the human IgG1 cDNA above (pUC18-Fc), which was digested with KpnI and SacII, deleting the CH1, hinge and part of CH2. The deleted region was replaced with a PCR amplified fragment containing the hinge-CH2 region as follows. Using the following PCR primers:

5' TCG AGC TCG GTA CCG AGC CCA AAT CGG CCG ACA AAA CTC ACA C 3' (SEQ ID NO:13)

and

5' GTA CTG CTC CTC CCG CGG CTT TGT CTT G 3' (SEQ ID NO:14)

A DNA fragment containing the hinge-CH2 region was amplified from pUC18-Fc, digested with KpnI and SacII, gel purified and cloned into the KpnI/SacII digested pUC18-Fc vector. The Cys, which occurs at position 230 (Kabat numbering; Kabat et al., "Sequences of Proteins of Immunological Interest, 5th Edition, US Department of Health and Human Services, NIH Publication No. 91-3242 (1991)) of the IgG1 heavy chain, was altered to an Ala through a TGT to GCC substitution in the nucleotide sequence. An altered DNA sequence in one of the PCR primers introduced a unique KpnI site at the 5' end of the hinge. The resulting plasmid was called pUC18Fcmod, and the junctions and PCR amplified region were sequenced for confirmation.

The entire hinge-CH2-CH3 insert in pUC18-Fcmod was removed in a single DNA fragment with KpnI and XbaI, gel purified, and ligated into SFcR1Cos4 cut with KpnI and XbaI to create COSFc.

SFcR1Cos4 is a derivative of pST4DHFR (Deen, K., McDougal, J. S., Inacker, R., Folena-Wasserman, G., Arthos, J., Rosenberg, J., Maddon, P. J., Axel, R., and Sweet, R. W. Nature 331: 82 [1988]) and contains the soluble Fc receptor type I (sFcR1) inserted between the cytomegalovirus (CMV) promoter and bovine growth hormone (BGH) polyadenylation regions, and also contains the dihydrofolate reductase (DHFR) cDNA inserted between the β-globin promoter and SV40 polyadenylation regions, an SV40 origin of replication, and an ampicillin resistance gene for growth in bacteria. Cutting the vector with KpnI and XbaI removes the sFcR1 coding region, so that the COSFc vector contains the hinge-CH2-CH3 region inserted between the CMV promoter and BGH polyA regions.

The COSFcLink vector was made from COSFc by inserting an oligonucleotide linker at the unique EcoRI site of the vector, which recreates this EcoRI site, and also introduces BstEII, PstI and EcoRV cloning sites. The oligonucleotides used were:

5' AATTCGGTTACCTGCAGATATCAAGCT 3' (SEQ ID NO:15)

3' GCCAATGGACGTCTATAGTTCGATTAA 5' (SEQ ID NO:16)

The junction was sequenced to confirm orientation in the vector. The size of the final vector is 6.37 kb.

(c) Construction of DNA coding for fusion protein.

To insert the IL4.Y124D cDNA, the COSFcLink vector was prepared by digesting with EcoRV and KpnI as follows: 5 μg DNA was incubated with 15 units EcoRV in react 2 at 37° C. for 5 hours, followed by ethanol precipitation. The resulting DNA was digested with KpnI in react 4 at 37° C. for 3 hours, and ethanol precipitated. The IL4.Y124D/SmaI/KpnI and the COSFcLink/EcoRV/KpnI fragments were ligated together to form plasmid pDB951, which encodes the IL4.Y124D/IgG1 fusion protein. The ligation was achieved using an Amersham DNA ligation kit, product code RPN 1507, the reactions being incubated at 16° C. overnight. The ligation reaction products were transformed into Promega JM109 competent cells (high efficiency) and plated onto Luria Broth agar containing ampicillin at 50 μg/ml. Transformants were cultured in Luria Broth (containing ampicillin at 50 μg/ml) and DNA prepared using Promega "Magic Minipreps". Production of an IL4.Y124D/COSFcLink recombinant DNA was verified by restriction digests and DNA sequencing. The complete IL4.Y124D sequence and the junctions with the COSFcLink DNA were confirmed by DNA sequencing (Table 2). The coding sequence of the recombinant IL4.Y124D/IgG1 DNA is shown in Table 3 and the amino acid sequence of the fusion protein is shown in Table 4. The IL4.Y124D/COSFcLink recombinant DNA was prepared and purified using caesium chloride gradients and the DNA used to transiently transfect HeLa cells.

2. Expression of the fusion protein

HeLa cells were grown in MEMα medium (Gibco) with 10% foetal calf serum and 1% glutamine. For the assay, $1 \times 10^6$ HeLa cells were seeded in 15 mls RPMI-1640 medium with 10% newborn calf serum, 1% glutamine ("seeding medium"), in a 75 cm² flask, four days prior to transfection. On the day prior to transfection, a further 12.5 mls seeding medium was added to each flask. On the day of transfection, the medium was changed to 15 mls of "transfection medium" (MEM medium with Earle's salts containing 10% newborn calf serum and 1% non essential amino acids), at time zero. At time +3 hours, 25 μg of the appropriate DNA in 0.125M $CaCl_2$, 1×HBS (HEPES buffered saline) was added to the cells. At time +7 hours, the cells were subjected to a glycerol shock (15%v/v) and then left to incubate overnight in 12.5 mls seeding medium containing 5 mM sodium butyrate. The next day the cells were washed with PBS (Dulbecco's phosphate buffered saline) and 12.5 mls "harvest medium" (RPMI-1640 with 2% of a 7.5% stock sodium bicarbonate solution) was added. After a further 24 hour incubation, the supernatants were removed, centrifuged at 1000 rpm for 5 minutes to remove cell debris and stored at either 4° C. or −20° C.

3. Biological Activity

For assay of supernatant for IL4 antagonist activity: using the method described in Spits et al., J. Immunology 139, 1142 (1987), human peripheral blood lymphocytes were incubated for three days with phytohaemagluttinin, a T cell mitogen, to upregulate the IL4 receptor. The resultant blast cells were then stimulated for a further three days with IL4. Proliferation was measured by the incorporation of 3H thymidine.

The IL4.Y124D/IgG1 chimera inhibited $^3H$ thymidine incorporation by human peripheral blood T lymphocytes stimulated with 133pM IL4 in a dose dependent manner.

EXAMPLE 2

IL4.Y124D/IgG4 fusion protein

1. Construction of DNA coding for fusion protein

PCR was performed to amplify the IL4.Y124D coding region and introduce a silent nucleotide substitution at the 3' end which creates a XhoI site. As substrate for the PCR reaction 20 ng of linearised pDB951 plasmid (Example 1.1(c)) was used. The oligonucleotide primers used were as follows:

1) 5' CAC AAG TGC GAT ATC ACC TTA CAG GAG ATC 3' (SEQ ID NO:17)

(includes an EcoRV restriction site, GATATC)

2) 5' CTC GGT ACC GCT CGA GCA CTT TGA GTC TTT 3' (SEQ ID NO:18)

(includes a XhoI restriction site, CTCGAG).

A second PCR reaction was performed to amplify the hinge-CH2-CH3 fragment of the human IgG4 heavy chain. The substrate for this was a synthetic human IgG4 heavy chain cDNA, the sequence of which is described in Table 5, and is based on the Genbank sequence GB:HUMIGCD2 (Ellison J., Buxbaum J. and Hood L. E., DNA 1:11–18, 1981). Numerous silent substitutions were made to the published nucleotide sequence. The gene was assembled by combining two 0.5 Kb synthetic DNA fragments. Each 0.5 Kb fragment was made by annealing a series of overlapping oligonucleotides and then filling in the gaps by PCR. The two 0.5 Kb fragments were joined at the SacII site and inserted into the pCR2 vector. A 1.0 Kb ApaI-BglII fragment containing the entire constant region was isolated and ligated into an expression vector, pCD, containing a humanized IL4 specific variable region. This construct was used as the PCR substrate to amplify the hinge-CH2-CH3 region of IgG4.

The oligonucleotide primers used for amplification of the IgG4 hinge-CH2-CH3 region were as follows:

1) 5' GGT GGA CAA CTC GAG CGA GTC CAA ATA TGG 3' (SEQ ID NO:19)

(includes a XhoI restriction site, CTCGAG)

2) 5' TTA CGT AGA TCT AGA CTA CAC TCA TTT ACC 3' (SEQ ID NO:20)

(includes an XbaI site, TCTAGA).

The conditions for both PCR reactions were as described for the derivation of pDB951. Briefly, primers were used at 5 ng/µl, and dNTPs at a final concentration of 0.2 mM in a total reaction volume of 100 µl. 2.5 Units of Taq polymerase enzyme from Advanced Biotechnologies were used and 31 cycles of PCR performed. Cycles consisted of a denaturation step of 1 minute at 94° C., an annealing step of 1 minute 30 seconds at 50° C., and an elongation step of 1 minute 30 seconds at 72° C. On cycle 1 denaturation was extended to 5 minutes and on the final cycle elongation was extended to 7 minutes.

PCR products of approximately 700 bp (hinge-CH2-CH3 of IgG4) and 400 bp (IL4.Y124D) were obtained and purified using the Promega "Magic PCR cleanup" kit. The purified PCR reactions were then digested with the following enzymes to create "sticky ends": XhoI and XbaI for IgG4 and EcoRV and XhoI for IL4.Y124D. The digests were incubated at 37° C. for 3 hours and then ethanol precipitated. The resulting DNAs were analysed by gel electrophoresis and gave sizes of approximately 690 bp (hinge-CH2-CH3 of IgG4) and 370bp (IL4.Y124D).

A vector was prepared into which to ligate the hinge-CH2-CH3 of IgG4 and IL4.Y124D PCR fragments by digesting pDB951 (IL4.Y124D in COSFcLink) with EcoRV and XbaI to remove most of the IL4.Y124D/IgG1 fusion molecule. The only part remaining is approximately 75 bp at the 5' end of IL4, which is not present in the IL4.Y124D EcoRV/XhoI fragment produced by PCR amplification. 5 µg of pDB951 DNA was digested in a total volume of 30 µl using react 2 buffer (GibcoBRL). The resulting 5.8 Kb DNA fragment was purified using the Geneclean™ procedure.

The three fragments described (IL4.Y124D EcoRV/XhoI, hinge-CH2-CH3 of IgG4 XhoI/XbaI and the 5.8 Kb fragment resulting from EcoRV/XbaI digestion of pDB951) were ligated together to form plasmid pDB952, which encodes the IL4.Y124D/IgG4 fusion protein. The ligation was carried out using a DNA ligation kit from Amersham (product code RPN 1507), incubating the reactions at 16° C. overnight. The ligation reaction products were transformed into Promega JM109 competent cells (high efficiency) and plated onto Luria Broth agar containing ampicillin at 50 µg/ml. Transformants were cultured in Luria Broth (containing ampicillin at 50 µg/ml) and DNA prepared using Promega "Magic Minipreps". Production of an IL4.Y124D/IgG4 recombinant DNA was verified by restriction digests, and the complete IL4.Y124D and hinge-CH2-CH3 IgG4 regions were verified by DNA sequencing. Table 6 describes the sequence of the coding region only of the IL4.Y124D/IgG4 fusion molecule, and Table 7 contains the amino acid sequence of the fusion protein. The IL4.Y124D/IgG4 recombinant DNA was prepared and purified using caesium chloride gradients and the DNA used to transiently transfect HeLa cells.

2. Expression of the fusion protein

HeLa cells were grown in MEMα medium (Gibco) with 10% foetal calf serum and 1% glutamine. For the assay, $1 \times 10^6$ HeLa cells were seeded in 15 mls RPMI-1640 medium with 10% newborn calf serum, 1% glutamine ("seeding medium"), in a 75cm$^2$ flask, four days prior to transfection. On the day prior to transfection, a further 12.5 mls seeding medium was added to each flask. On the day of transfection, the medium was changed to 15 mls of "transfection medium" (MEM medium with Earle's salts containing 10% newborn calf serum and 1% non essential amino acids), at time zero. At time +3 hours, 25 µg of the appropriate DNA in 0.125M CaCl$_2$, 1×HBS (HEPES buffered saline) was added to the cells. At time +7 hours, the cells were subjected to a glycerol shock (15%v/v) and then left to incubate overnight in 12.5 mls seeding medium containing 5 mM sodium butyrate. The next day the cells were washed with PBS (Dulbecco's phosphate buffered saline) and 12.5 mls "harvest medium" (RPMI-1640 with 2% of a 7.5% stock sodium bicarbonate solution) was added. After a further 24 hour incubation, the supernatants were removed, centrifuged at 1000 rpm for 5 minutes to remove cell debris and stored at either 4° C. or −20° C.

3. Biological Activity

For assay of supernatant for IL4 antagonist activity: using the method described in Spits et al., J. Immunology 139, 1142 (1987), human peripheral blood lymphocytes were incubated for three days with phytohaemagluttinin, a T cell mitogen, to upregulate the IL4 receptor. The resultant blast cells were then stimulated for a further three days with IL4. Proliferation was measured by the incorporation of 3H thymidine.

The IL4.Y124D/IgG4 chimera inhibited $^3$H thymidine incorporation by human peripheral blood T lymphocytes stimulated with 133pM IL4 in a dose dependent manner.

EXAMPLE 3

IL4.Y124D/IgG4 PE fusion protein

1. Construction of DNA coding for fusion protein

PCR is performed to amplify the IL4.Y124D coding region and introduce a silent nucleotide substitution at the 3' end which creates a XhoI site as described in Example 2.

A second PCR reaction is performed to amplify the hinge-CH2-CH3 fragment of the human IgG4 heavy chain PE variant. In IgG4 PE, residue 10 of the hinge (residue 241, Kabat numbering) is altered from serine (S) in the wild type to proline (P) and residue 5 of CH2 (residue 248, Kabat numbering) is altered from leucine (L) in the wild type to glutamate (E). Angal S., King D. J., Bodmer M. W., Turner A., Lawson A. D. G., Roberts G., Pedley B. and Adair R., Molecular Immunology vol30pp105–108, 1993, describe an IgG4 molecule where residue 241 (Kabat numbering) is altered from serine to proline. This change increases the serum half-life of the IgG4 molecule.

The IgG4 PE variant was created using PCR mutagenesis on the synthetic human IgG4 heavy chain cDNA described in Table 5, and was then ligated into the pCD expression vector. It was this plasmid which was used as the substrate for the PCR reaction amplifying the hinge-CH2-CH3 fragment of IgG4 PE. The sequence of the IgG4 PE variant is described in Table 8. The residues of the IgG4 nucleotide sequence which were altered to make the PE variant are as follows:

referring to Table 8:

- residue 322 has been altered to "C" in the PE variant from "T" in the wild type;
- residue 333 has been altered to "G" in the PE variant from "A" in the wild type; and
- residues 343–344 have been altered to "GA" in the PE variant from "CT" in the wild type.

Oligonucleotide primers are used for amplification of the IgG4 PE variant hinge-CH2-CH3 region as described for the derivation of pDB952.

PCR products of approximately 700 bp (hinge-CH2-CH3 of IgG4 PE mutant) and 400 bp (IL4.Y124D) are obtained and purified using the Promega "Magic PCR cleanup" kit. The purified PCR reactions are then digested with the following enzymes to create "sticky ends": XhoI and XbaI for IgG4 PE and EcoRV and XhoI for IL4.Y124D. The digests are incubated at 37° C. for 3 hours and then ethanol precipitated. The resulting DNAs are of sizes of approximately 690 bp (hinge-CH2-CH3 of IgG4 PE) and 370bp (IL4.Y124D).

To obtain larger amounts of the IgG4 PE variant hinge-CH2-CH3 fragment and the IL4.Y124D fragment, the purified and digested PCR products are ligated into Bluescript KS+™ which is prepared by digestion with either XhoI and XbaI for the hinge-CH2-CH3 of IgG4 PE fragment or EcoRV and XhoI for the IL4.Y124D fragment, followed by Geneclean™. A Bluescript KS+/hinge-CH2-CH3 of IgG4 PE recombinant and a Bluescript KS+/IL4.Y124D recombinant are thus generated. Large amounts of these DNAs are produced using the Promega "Magic Maxiprep" method. The IgG4 PE hinge-CH2-CH3 fragment is excised from the Bluescript recombinant using XhoI and XbaI. The resulting fragment of approximately 690 bp is purified by Geneclean™ to generate large amounts of the IgG4 PE hinge-CH2-CH3 XhoI/XbaI fragment. The IL4.Y124D fragment is excised from the Bluescript recombinant using EcoRV and XhoI and the resulting fragment of approximately 370 bp is purified by Geneclean™.

A vector is prepared into which to ligate the hinge-CH2-CH3 of IgG4 PE and IL4.Y124D fragments by digesting pDB951 with EcoRV and XbaI as described for the derivation of pDB952.

The three fragments described (IL4.Y124D EcoRV/XhoI, hinge-CH2-CH3 of IgG4 PE variant XhoI/XbaI and the 5.8 Kb fragment resulting from EcoRV/XbaI digestion of pDB951) are ligated together to form plasmid pDB953 using a DNA ligation kit from Amersham (product code RPN 1507), incubating the reactions at 16° C. overnight. The ligation reaction products are transformed into Promega JM109 competent cells (high efficiency) and plated onto Luria Broth agar containing ampicillin at 50 μg/ml. Transformants are cultured in Luria Broth (containing ampicillin at 50 μg/ml) and DNA prepared using Promega "Magic Minipreps". Production of an IL4.Y124D/IgG4 PE variant recombinant DNA is verified by restriction digests, and the complete IL4.Y124D and hinge-CH2-CH3 IgG4 PE variant regions are verified by DNA sequencing. Table 9 describes the sequence of the coding region only of the IL4. Y124D/IgG4 PE fusion molecule, and Table 10 contains the amino acid sequence of the fusion protein. The IL4.Y124D/IgG4 PE recombinant DNA is prepared and purified using caesium chloride gradients and the DNA used to transiently transfect HeLa cells.

2. Expression of the fusion protein

HeLa cells were grown in MEMα medium (Gibco) with 10% foetal calf serum and 1% glutamine. For the assay, $1\times10^6$ HeLa cells were seeded in 15mls RPMI-1640 medium with 10% newborn calf serum, 1% glutamine ("seeding medium"), in a 75 $cm^2$ flask, four days prior to transfection. On the day prior to transfection, a further 12.5 mls seeding medium was added to each flask. On the day of transfection, the medium was changed to 15 mls of "transfection medium" (MEM medium with Earle's salts containing 10% newborn calf serum and 1% non essential amino acids), at time zero. At time +3 hours, 25 μg of the appropriate DNA in 0. 125M $CaCl_2$, 1×HBS (HEPES buffered saline) was added to the cells. At time +7 hours, the cells were subjected to a glycerol shock (15% v/v) and then left to incubate overnight in 12.5 mls seeding medium containing 5 mM sodium butyrate. The next day the cells were washed with PBS (Dulbecco's phosphate buffered saline) and 12.5 mls "harvest medium" (RPMI-1640 with 2% of a 7.5% stock sodium bicarbonate solution) was added. After a further 24 hour incubation, the supernatants were removed, centrifuged at 1000 rpm for 5 minutes to remove cell debris and stored at either 4° C. or −20° C.

3. Biological Activity

For assay of supernatant for IL4 antagonist activity: using the method described in Spits et al., J. Immunology 139, 1142 (1987), human peripheral blood lymphocytes were incubated for three days with phytohaemagluttinin, a T cell mitogen, to upregulate the IL4 receptor. The resultant blast cells were then stimulated for a further three days with IL4. Proliferation was measured by the incorporation of 3H thymidine.

The IL4.Y124D/IgG4 PE chimera inhibited ³H thymidine incorporation by human peripheral blood T lymphocytes stimulated with 133pM IL4 in a dose dependent manner.

EXAMPLE 4
Mammalian Expression vector containing DNA coding for IL4.Y124D/IgG4 PE 1. Construction of DNA The pCDN vector (Aiyar, N., Baker, E., Wu, H.-L., Nambi, P., Edwards, R. M., Trill, J. J., Ellis, C., Bergsma, D. Molecular and Cellular Biochemistry 131:75–86, 1994) contains the CMV promoter, a polylinker cloning region, and the BGH polyadenylation region. This vector also contains a bacterial neomycin phosphotransferase gene (NEO) inserted between the β-globin promoter and SV40 polyadenylation region for Geneticin™ selection, the DHFR selection cassette inserted between the β-globin promoter and BGH polydenylation region for methotrexate (MTX) amplification, an ampicillin resistance gene for growth in bacteria, and a SV40 origin of replication.

To insert the IL4.Y124D/IgG4 PE cDNA, the pCDN vector was prepared by digesting with Nde1 and BstX1 as follows: 15 μg of DNA was incubated with 30 units of BstX1 in react 2 (Gibco-BRL) at 55° C. for 1 hour, and ethanol precipitated. The resulting DNA was digested with Nde1 in react 2 at 37° C. for 1 hour, and ethanol precipitated. The IL4.Y124D/IgG4 PE fragment was prepared from pDB953 (Example 3.1) by digesting with BstX1 and Nde1 as follows: 15μg of DNA was incubated with 30 units of BstX1 in react 2 at 55° C. for 1 hour, and ethanol precipitated. The resulting DNA was digested with Nde1 in react 2 at 37° C. for 1 hour, and ethanol precipitated.

The IL4.Y124D/IgG4 PE Nde1/BstX1 and pCDN Nde1/BstX1 fragments were ligated together to form the plasmid pCDN-IL4.Y124D/IgG4 PE. The ligation was achieved using 2 units of T4 DNA Ligase (Gibco BRL) with T4 DNA Ligase buffer. The reactions were incubated at 16° C. overnight. The ligation reaction products were transformed into Gibco-BRL DH5a competent cells (subcloning efficiency) and plated onto Luria Broth agar containing 75 ug/ml ampicillin. Transformants were cultured in Luria Broth (containing ampicillin at 50 ug/ml) and DNA prepared by alkaline lysis. Production of a pCDN-IL4.Y124D/IgG4 PE DNA was confirmed by restriction digests. The complete sequence of the recombinant IL4.Y124D/IgG4 PE DNA was confirmed by sequencing. The pCDN-IL4.Y124D/IgG4 PE recombinant DNA was prepared and purified using Qiagen columns and the DNA was used to transiently infect COS cells and electroporated into CHO cells to create stable clones.

2. Expression of the Fusion Protein a) Transient Expression in COS

COS-1 cells were grown in DMEM medium with 10% fetal bovine serum. For the transfection, cells were seeded at $2\times10^{5}$ cells into a 35 mm tissue culture dish 24 hours prior. A solution containing 1 μg of DNA in 100 μl of DMEM without serum is added to a solution containing 6 μl of LIPOFECTAMINE Reagent (Gibco-BRL) in 100 μl of DMEM without serum, gently swirled and incubated at room temperature for 45 minutes. The cells are washed once with serum free DMEM. 0.8ml of serum free DMEM is added to the DNA-LIPOFECTAMINE SOLUTION, mixed gently and the diluted solution is overlayed on the cells. The cells are incubated at 37° C. for 5 hours, then 1 ml of DMEM containing 20% fetal bovine serum is added. The cells are assayed 48–72 hours later to determine expression levels.

b) Electroporation into CHO cells

CHO cells, ACC-098 (a suspension cell line derived from CHO DG-44, Urlaub, G., Kas, E., Carothers, A. M. and Chasin, L. A. Cell, 33, 405–412, 1983) were grown in serum free growth medium WO 92/05246. 15 μg of the pCDN-IL4.Y124D/IgG4 PE plasmid was digested using 30 units of Not1 at 37° C. for 3 hours to linearize the plasmid, and precipitated with ethanol. The resulting DNA was resuspended in 50 ul of 1×TE (10 mM Tris, pH 8.0, 1 mM EDTA). The DNA was electroporated into $1\times10^{7}$ ACC-098 cells, using a Bio Rad Gene Pulser set at 380V and 25 μFd. The cells were resuspended into growth medium at $2.5\times10^{4}$ cells/ml, and 200 μl of the cell suspension was plated into each well of a 96 well plate. 48 hours later the medium was switched to growth medium containing 400 μg/ml G418 (Geneticin). Twenty one days post selection, conditioned medium from the colonies which arose were screened by Elisa assay. The highest expressing colonies were transferred to 24 well plates in order to be scaled up.

TABLE 1

DNA sequence of COSFcLink vector, 6367bp

SEQ ID No: 1

| | |
|---|---|
| GACGTCGACGGATCGGGAGATCGGGGATCGATCCGTCGACGTACGACTAGTTATTAATAG | 60 |
| TAATCAATTACGGGGTCATTAGTTCATAGCCCATATATGGAGTTCCGCGTTACATAACTT | 120 |
| ACGGTAAATGGCCCGCCTGGCTGACCGCCCAACGACCCCCGCCCATTGACGTCAATAATG | 180 |
| ACGTATGTTCCCATAGTAACGCCAATAGGGACTTTCCATTGACGTCAATGGGTGGACTAT | 240 |
| TTACGGTAAACTGCCCACTTGGCAGTACATCAAGTGTATCATATGCCAAGTACGCCCCCT | 300 |
| ATTGACGTCAATGACGGTAAATGGCCCGCCTGGCATTATGCCCAGTACATGACCTTATGG | 360 |
| GACTTTCCTACTTGGCAGTACATCTACGTATTAGTCATCGCTATTACCATGGTGATGCGG | 420 |
| TTTTGGCAGTACATCAATGGGCGTGGATAGCGGTTTGACTCACGGGGATTTCCAAGTCTC | 480 |
| CACCCCATTGACGTCAATGGGAGTTTGTTTTGGCACCAAAATCAACGGGACTTTCCAAAA | 540 |
| TGTCGTAACAACTCCGCCCCATTGACGCAAATGGGCGGTAGGCGTGTACGGTGGGAGGTC | 600 |
| TATATAAGCAGAGCTGGGTACGTGAACCGTCAGATCGCCTGGAGACGCCATCGAATTCGG | 660 |
| TTACCTGCAGATATCAAGCTAATTCGGTACCGAGCCCAAATCGGCCGACAAAACTCACAC | 720 |
| ATGCCCACCGTGCCCAGCACCTGAACTCCTGGGGGGACCGTCAGTCTTCCTCTTCCCCCC | 780 |
| AAAACCCAAGGACACCCTCATGATCTCCCGGACCCCTGAGGTCACATGCGTGGTGGTGGA | 840 |
| CGTGAGCCACGAAGACCCTGAGGTCAAGTTCAACTGGTACGTGGACGGCGTGGAGGTGCA | 900 |
| TAATGCCAAGACAAAGCCGCGGGAGGAGCAGTACAACAGCACGTACCGGGTGGTCAGCGT | 960 |
| CCTCACCGTCCTGCACCAGGACTGGCTGAATGGCAAGGAGTACAAGTGCAAGGTCTCCAA | 1020 |
| CAAAGCCCTCCCAGCCCCCATCGAGAAAACCATCTCCAAAGCCAAAGGGCAGCCCCGAGA | 1080 |
| ACCACAGGTGTACACCCTGCCCCCATCCCGGGATGAGCTGACCAAGAACCAGGTCAGCCT | 1140 |
| GACCTGCCTGGTCAAAGGCTTCTATCCCAGCGACATCGCCGTGGAGTGGGAGAGCAATGG | 1200 |

TABLE 1-continued

DNA sequence of COSFcLink vector, 6367bp

SEQ ID No: 1

| Sequence | Position |
|---|---|
| GCAGCCGGAGAACAACTACAAGACCACGCCTCCCGTGCTGGACTCCGACGGCTCCTTCTT | 1260 |
| CCTCTACAGCAAGCTCACCGTGGACAAGAGCAGGTGGCAGCAGGGGAACGTCTTCTCATG | 1320 |
| CTCCGTGATGCATGAGGCTCTGCACAACCACTACACGCAGAAGAGCCTCTCCCTGTCTCC | 1380 |
| GGGTAAATGAGTGTAGTCTAGAGCTCGCTGATCAGCCTCGACTGTGCCTTCTAGTTGCCA | 1440 |
| GCCATCTGTTGTTTGCCCCTCCCCCGTGCCTTCCTTGACCCTGGAAGGTGCCACTCCCAC | 1500 |
| TGTCCTTTCCTAATAAAATGAGGAAATTGCATCGCATTGTCTGAGTAGGTGTCATTCTAT | 1560 |
| TCTGGGGGGTGGGGTGGGGCAGGACAGCAAGGGGGAGGATTGGGAAGACAATAGCAGGCA | 1620 |
| TGCTGGGGATGCGGTGGGCTCTATGGAACCAGCTGGGGCTCGAGGGGGGATCTCCCGATC | 1680 |
| CCCAGCTTTGCTTCTCAATTTCTTATTTGCATAATGAGAAAAAAAGGAAAATTAATTTTA | 1740 |
| ACACCAATTCAGTAGTTGATTGAGCAAATGCGTTGCCAAAAAGGATGCTTTAGAGACAGT | 1800 |
| GTTCTCTGCACAGATAAGGACAAACATTATTCAGAGGGAGTACCCAGAGCTGAGACTCCT | 1860 |
| AAGCCAGTGAGTGGCACAGCATTCTAGGGAGAAATATGCTTGTCATCACCGAAGCCTGAT | 1920 |
| TCCGTAGAGCCACACCTTGGTAAGGGCCAATCTGCTCACACAGGATAGAGAGGGCAGGAG | 1980 |
| CCAGGGCAGAGCATATAAGGTGAGGTAGGATCAGTTGCTCCTCACATTTGCTTCTGACAT | 2040 |
| AGTTGTGTTGGGAGCTTGGATAGCTTGGACAGCTCAGGGCTGCGATTTCGCGCCAAACTT | 2100 |
| GACGGCAATCCTAGCGTGAAGGCTGGTAGGATTTTATCCCCGCTGCCATCATGGTTCGAC | 2160 |
| CATTGAACTGCATCGTCGCCGTGTCCCAAAATATGGGGATTGGCAAGAACGGAGACCTAC | 2220 |
| CCTGGCCTCCGCTCAGGAACGAGTTCAAGTACTTCCAAAGAATGACCACAACCTCTTCAG | 2280 |
| TGGAAGGTAAACAGAATCTGGTGATTATGGGTAGGAAAACCTGGTTCTCCATTCCTGAGA | 2340 |
| AGAATCGACCTTTAAAGGACAGAATTAATATAGTTCTCAGTAGAGAACTCAAAGAACCAC | 2400 |
| CACGAGGAGCTCATTTTCTTGCCAAAAGTTTGGATGATGCCTTAAGACTTATTGAACAAC | 2460 |
| CGGAATTGGCAAGTAAAGTAGACATGGTTTGGATAGTCGGAGGCAGTTCTGTTTACCAGG | 2520 |
| AAGCCATGAATCAACCAGGCCACCTTAGACTCTTTGTGACAAGGATCATGCAGGAATTTG | 2580 |
| AAAGTGACACGTTTTTCCCAGAAATTGATTTGGGGAAATATAAACTTCTCCCAGAATACC | 2640 |
| CAGGCGTCCTCTCTGAGGTCCAGGAGGAAAAAGGCATCAAGTATAAGTTTGAAGTCTACG | 2700 |
| AGAAGAAAGACTAACAGGAAGATGCTTTCAAGTTCTCTGCTCCCCTCCTAAAGCTATGCA | 2760 |
| TTTTTATAAGACCATGCTAGCTTGAACTTGTTTATTGCAGCTTATAATGGTTACAAATAA | 2820 |
| AGCAATAGCATCACAAATTTCACAAATAAAGCATTTTTTTCACTGCATTCTAGTTGTGGT | 2880 |
| TTGTCCAAACTCATCAATGTATCTTATCATGTCTGGATCAACGATAGCTTATCTGTGGGC | 2940 |
| GATGCCAAGCACCTGGATGCTGTTGGTTTCCTGCTACTGATTTAGAAGCCATTTGCCCCC | 3000 |
| TGAGTGGGGCTTGGGAGCACTAACTTTCTCTTTCAAAGGAAGCAATGCAGAAAGAAAAGC | 3060 |
| ATACAAAGTATAAGCTGCCATGTAATAATGGAAGAAGATAAGGTTGTATGAATTAGATTT | 3120 |
| ACATACTTCTGAATTGAAACTAAACACCTTTAAATTCTTAAATATATAACACATTTCATA | 3180 |
| TGAAAGTATTTTACATAAGTAACTCAGATACATAGAAAACAAAGCTAATGATAGGTGTCC | 3240 |
| CTAAAAGTTCATTTATTAATTCTACAAATGATGAGCTGGCCATCAAAATTCCAGCTCAAT | 3300 |
| TCTTCAACGAATTAGAAAGAGCAATCTGCAAACTCATCTGGAATAACAAAAAACCTAGGA | 3360 |
| TAGCAAAAACTCTTCTCAAGGATAAAAGAACCTCTGGTGGAATCACCATGCCTGACCTAA | 3420 |
| AGCTGTACTACAGAGCAATTGTGATAAAAACTGCATGGTACTGATATAGAAACGGACAAG | 3480 |
| TAGACCAATGGAATAGAACCCACACACCTATGGTCACTTGATCTTCAACAAGAGAGCTAA | 3540 |
| AACCATCCACTGGAAAAAAGACAGCATTTTCAACAAATGGTGCTGGCACAACTGGTGGTT | 3600 |
| ATCATGGAGAAGAATGTGAATTGATCCATTCCAATCTCCTTGTACTAAGGTCAAATCTAA | 3660 |
| GTGGATCAAGGAACTCCACATAAAACCAGAGACACTGAAACTTATAGAGGAGAAAGTGGG | 3720 |
| GAAAAGCCTCGAAGATATGGGCACAGGGGAAAAATTCCTGAATAGAACAGCAATGGCTTG | 3780 |
| TGCTGTAAGATCGAGAATTGACAAATGGGACCTCATGAAACTCCAAAGCTATCGGATCAA | 3840 |
| TTCCTCCAAAAAAGCCTCCTCACTACTTCTGGAATAGCTCAGAGGCCGAGGCGGCCTCGG | 3900 |
| CCTCTGCATAAATAAAAAAAATTAGTCAGCCATGCATGGGGCGGAGAATGGGCGGAACTG | 3960 |
| GGCGGAGTTAGGGGCGGGATGGGCGGAGTTAGGGGCGGACTATGGTTGCTGACTAATTG | 4020 |
| AGATGCATGCTTTGCATACTTCTGCCTGCTGGGGAGCCTGGGGACTTTCCACACCTGGTT | 4080 |
| GCTGACTAATTGAGATGCATGCTTTGCATACTTCTGCCTGCTGGGGAGCCTGGGGACTTT | 4140 |
| CCACACCCTAACTGACACACATTCCACAGAATTAATTCCCGATCCCGTCGACCTCGAGAG | 4200 |
| CTTGGCGTAATCATGGTCATAGCTGTTTCCTGTGTGAAATTGTTATCCGCTCACAATTCC | 4260 |
| ACACAACATACGAGCCGGAAGCATAAAGTGTAAAGCCTGGGGTGCCTAATGAGTGAGCTA | 4320 |
| ACTCACATTAATTGCGTTGCGCTCACTGCCCGCTTTCCAGTCGGGAAACCTGTCGTGCCA | 4380 |
| GCTGCATTAATGAATCGGCCAACGCGCGGGGAGAGGCGGTTTGCGTATTGGGCGCTCTTC | 4440 |
| CGCTTCCTCGCTCACTGACTCGCTGCGCTCGGTCGTTCGGCTGCGGCGAGCGGTATCAGC | 4500 |
| TCACTCAAAGGCGGTAATACGGTTATCCACAGAATCAGGGGATAACGCAGGAAAGAACAT | 4560 |
| GTGAGCAAAAGGCCAGCAAAAGGCCAGGAACCGTAAAAAGGCCGCGTTGCTGGCGTTTTT | 4620 |
| CCATAGGCTCCGCCCCCCTGACGAGCATCACAAAAATCGACGCTCAAGTCAGAGGTGGCG | 4680 |
| AAACCCGACAGGACTATAAAGATACCAGGCGTTTCCCCCTGGAAGCTCCCTCGTGCGCTC | 4740 |
| TCCTGTTCCGACCCTGCCGCTTACCGGATACCTGTCCGCCTTTCTCCCTTCGGGAAGCGT | 4800 |
| GGCGCTTTCTCAATGCTCACGCTGTAGGTATCTCAGTTCGGTGTAGGTCGTTCGCTCCAA | 4860 |
| GCTGGGCTGTGTGCACGAACCCCCCGTTCAGCCCGACCGCTGCGCCTTATCCGGTAACTA | 4920 |
| TCGTCTTGAGTCCAACCCGGTAAGACACGACTTATCGCCACTGGCAGCAGCCACTGGTAA | 4980 |
| CAGGATTAGCAGAGCGAGGTATGTAGGCGGTGCTACAGAGTTCTTGAAGTGGTGGCCTAA | 5040 |
| CTACGGCTACACTAGAAGGACAGTATTTGGTATCTGCGCTCTGCTGAAGCCAGTTACCTT | 5100 |
| CGGAAAAAGAGTTGGTAGCTCTTGATCCGGCAAACAAACCACCGCTGGTAGCGGTGGTTT | 5160 |
| TTTTGTTTGCAAGCAGCAGATTACGCGCAGAAAAAAAGGATCTCAAGAAGATCCTTTGAT | 5220 |
| CTTTTCTACGGGGTCTGACGCTCAGTGGAACGAAAACTCACGTTAAGGGATTTTGGTCAT | 5280 |
| GAGATTATCAAAAAGGATCTTCACCTAGATCCTTTTAAATTAAAAATGAAGTTTTAAATC | 5340 |
| AATCTAAAGTATATATGAGTAAACTTGGTCTGACAGTTACCAATGCTTAATCAGTGAGGC | 5400 |
| ACCTATCTCAGCGATCTGTCTATTTCGTTCATCCATAGTTGCCTGACTCCCCGTCGTGTA | 5460 |
| GATAACTACGATACGGGAGGGCTTACCATCTGGCCCCAGTGCTGCAATGATACCGCGAGA | 5520 |
| CCCACGCTCACCGGCTCCAGATTTATCAGCAATAAACCAGCCAGCCGGAAGGGCCGAGCG | 5580 |
| CAGAAGTGGTCCTGCAACTTTATCCGCCTCCATCCAGTCTATTAATTGTTGCCGGGAAGC | 5640 |
| TAGAGTAAGTAGTTCGCCAGTTAATAGTTTGCGCAACGTTGTTGCCATTGCTACAGGCAT | 5700 |

TABLE 1-continued

DNA sequence of COSFcLink vector, 6367bp

SEQ ID No: 1

| | |
|---|---|
| CGTGGTGTCACGCTCGTCGTTTGGTATGGCTTCATTCAGCTCCGGTTCCCAACGATCAAG | 5760 |
| GCGAGTTACATGATCCCCCATGTTGTGCAAAAAAGCGGTTAGCTCCTTCGGTCCTCCGAT | 5820 |
| CGTTGTCAGAAGTAAGTTGGCCGCAGTGTTATCACTCATGGTTATGGCAGCACTGCATAA | 5880 |
| TTCTCTTACTGTCATGCCATCCGTAAGATGCTTTTCTGTGACTGGTGAGTACTCAACCAA | 5940 |
| GTCATTCTGAGAATAGTGTATGCGGCGACCGAGTTGCTCTTGCCCGGCGTCAATACGGGA | 6000 |
| TAATACCGCGCCACATAGCAGAACTTTAAAAGTGCTCATCATTGGAAAACGTTCTTCGGG | 6060 |
| GCGAAAACTCTCAAGGATCTTACCGCTGTTGAGATCCAGTTCGATGTAACCCACTCGTGC | 6120 |
| ACCCAACTGATCTTCAGCATCTTTTACTTTCACCAGCGTTTCTGGGTGAGCAAAAACAGG | 6180 |
| AAGGCAAAATGCCGCAAAAAAGGGAATAAGGGCGACACGGAAATGTTGAATACTCATACT | 6240 |
| CTTCCTTTTTCAATATTATTGAAGCATTTATCAGGGTTATTGTCTCATGAGCGGATACAT | 6300 |
| ATTTGAATGTATTTAGAAAAATAAACAAATAGGGGTTCCGCGCACATTTCCCCGAAAAGT | 6360 |
| GCCACCT | 6367 |

TABLE 2

DNA sequence of encoded Y124D-IgG1 fusion molecule in COSFcLink vector, 6926bp SEQ ID No: 2

| | |
|---|---|
| GACGTCGACGGATCGGGAGATCGGGGATCGATCCGTCGACGTACGACTAGTTATTAATAG | 60 |
| TAATCAATTACGGGGTCATTAGTTCATAGCCCATATATGGAGTTCCGCGTTACATAACTT | 120 |
| ACGGTAAATGGCCCGCCTGGCTGACCGCCCAACGACCCCCGCCCATTGACGTCAATAATG | 180 |
| ACGTATGTTCCCATAGTAACGCCAATAGGGACTTTCCATTGACGTCAATGGGTGGACTAT | 240 |
| TTACGGTAAACTGCCCACTTGGCAGTACATCAAGTGTATCATATGCCAAGTACGCCCCCT | 300 |
| ATTGACGTCAATGACGGTAAATGGCCCGCCTGGCATTATGCCCAGTACATGACCTTATGG | 360 |
| GACTTTCCTACTTGGCAGTACATCTACGTATTAGTCATCGCTATTACCATGGTGATGCGG | 420 |
| TTTTGGCAGTACATCAATGGGCGTGGATAGCGGTTTGACTCACGGGGATTTCCAAGTCTC | 480 |
| CACCCCATTGACGTCAATGGGAGTTTGTTTTGGCACCAAAATCAACGGGACTTTCCAAAA | 540 |
| TGTCGTAACAACTCCGCCCCATTGACGCAAATGGGCGGTAGGCGTGTACGGTGGGAGGTC | 600 |
| TATATAAGCAGAGCTGGGTACGTGAACCGTCAGATCGCCTGGAGACGCCATCGAATTCGG | 660 |
| TTACCTGCAGATGGGCTGCAGGAATTCCGCATTGCAGAGATAATTGTATTTAAGTGCCTA | 720 |
| GCTCGATACAATAAACGCCATTTGACCATTCACCACATTGGTGTGCACCTCCAAGCTTAC | 780 |
| CTGCCATGGGTCTCACCTCCCAACTGCTTCCCCCTCTGTTCTTCCTGCTAGCATGTGCCG | 840 |
| GCAACTTTGTCCACGGACACAAGTGCGATATCACCTTACAGGAGATCATCAAAACTTTGA | 900 |
| ACAGCCTCACAGAGCAGAAGACTCTGTGCACCGAGTTGACCGTAACAGACATCTTTGCTG | 960 |
| CCTCCAAGAACACAACTGAGAAGGAAACCTTCTGCAGGGCTGCGACTGTGCTCCGGCAGT | 1020 |
| TCTACAGCCACCATGAGAAGGACACTCGCTGCCTGGGTGCGACTGCACAGCAGTTCCACA | 1080 |
| GGCACAAGCAGCTGATCCGATTCCTGAAACGGCTCGACAGGAACCTCTGGGGCCTGGCGG | 1140 |
| GCTTGAATTCCTGTCCTGTGAAGGAAGCCAACCAGAGTACGTTGGAAAACTTCTTGGAAA | 1200 |
| GGCTAAAGACGATCATGAGAGAGAAAGACTCAAAGTGTTCGAGCGTACCGAGCCCAAAT | 1260 |
| CGGCCGACAAAACTCACACATGCCCACCGTGCCCAGCACCTGAACTCCTGGGGGGACCGT | 1320 |
| CAGTCTTCCTCTTCCCCCCAAAACCCAAGGACACCCTCATGATCTCCCGGACCCCTGAGG | 1380 |
| TCACATGCGTGGTGGTGGACGTGAGCCACGAAGACCCTGAGGTCAAGTTCAACTGGTACG | 1440 |
| TGGACGGCGTGGAGGTGCATAATGCCAAGACAAAGCCGCGGGAGGCAGTACAACAGCA | 1500 |
| CGTACCGGGTGGTCAGCGTCCTCACCGTCCTGCACCAGGACTGGCTGAATGGCAAGGAGT | 1560 |
| ACAAGTGCAAGGTCTCCAACAAAGCCCTCCCAGCCCCCATCGAGAAAACCATCTCCAAAG | 1620 |
| CCAAAGGGCAGCCCCGAGAACCACAGGTGTACACCCTGCCCCCATCCCGGGATGAGCTGA | 1680 |
| CCAAGAACCAGGTCAGCCTGACCTGCCTGGTCAAAGGCTTCTATCCCAGCGACATCGCCG | 1740 |
| TGGAGTGGGAGAGCAATGGGCAGCCGGAGAACAACTACAAGACCACGCCTCCCGTGCTGG | 1800 |
| ACTCCGACGGCTCCTTCTTCCTCTACAGCAAGCTCACCGTGGACAAGAGCAGGTGGCAGC | 1860 |
| AGGGGAACGTCTTCTCATGCTCCGTGATGCATGAGGCTCTGCACAACCACTACACGCAGA | 1920 |
| AGAGCCTCTCCCTGTCTCCGGGTAAATGAGTGTAGTCTAGAGCTCGCTGATCAGCCTCGA | 1980 |
| CTGTGCCTTCTAGTTGCCAGCCATCTGTTGTTTGCCCCTCCCCCGTGCCTTCCTTGACCC | 2040 |
| TGGAAGGTGCCACTCCCACTGTCCTTTCCTAATAAAATGAGGAAATTGCATCGCATTGTC | 2100 |
| TGAGTAGGTGTCATTCTATTCTGGGGGGTGGGGTGGGGCAGGACAGCAAGGGGGAGGATT | 2160 |
| GGGAAGACAATAGCAGGCATGCTGGGGATGCGGTGGGCTCTATGGAACCAGCTGGGGCTC | 2220 |
| GAGGGGGGATCTCCCGATCCCCAGCTTTGCTTCTCAATTTCTTATTTGCATAATGAGAAA | 2280 |
| AAAAGGAAAATTAATTTTAACACCAATTCAGTAGTTGATTGAGCAAATGCGTTGCCAAAA | 2340 |
| AGGATGCTTTAGAGACAGTGTTCTCTGCACAGATAAGGACAAACATTATTCAGAGGGAGT | 2400 |
| ACCCAGAGCTGAGACTCCTAAGCCAGTGAGTGGCACAGCATTCTAGGGAGAAATATGCTT | 2460 |
| GTCATCACCGAAGCCTGATTCCGTAGAGCCACACCTTGGTAAGGGCCAATCTGCTCACAC | 2520 |
| AGGATAGAGAGGGCAGGAGCCAGGGCAGAGCATATAAGGTGAGGTAGGATCAGTTGCTCC | 2580 |
| TCACATTTGCTTCTGACATAGTTGTGTTGGGAGCTTGGATAGCTTGGACAGCTCAGGGCT | 2640 |
| GCGATTTCGCGCCAAACTTGACGGCAATCCTAGCGTGAAGGCTGGTAGGATTTTATCCCC | 2700 |
| GCTGCCATCATGGTTCGACCATTGAACTGCATCGTCGCCGTGTCCCAAAATATGGGGATT | 2760 |
| GGCAAGAACGGAGACCTACCCTGGCCTCCGCTCAGGAACGAGTTCAAGTACTTCCAAAGA | 2820 |
| ATGACCACAACCTCTTCAGTGGAAGGTAAACAGAATCTGGTGATTATGGGTAGGAAAACC | 2880 |
| TGGTTCTCCATTCCTGAGAAGAATCGACCTTTAAAGGACAGAATTAATATAGTTCTCAGT | 2940 |
| AGAGAACTCAAAGAAdCACCACGAGGAGCTCATTTTCTTGCCAAAAGTTTGGATGATGCC | 3000 |
| TTAAGACTTATTGAACAACCGGAATTGGCAAGTAAAGTAGACATGGTTTGGATAGTCGGA | 3060 |
| GGCAGTTCTGTTTACCAGGAAGCCATGAATCAACCAGGCCACCTTAGACTCTTTGTGACA | 3120 |
| AGGATCATGCAGGAATTTGAAAGTGACACGTTTTTCCCAGAAATTGATTTGGGGAAATAT | 3180 |

TABLE 2-continued

DNA sequence of encoded Y124D-IgG1 fusion molecule in COSFcLink vector, 6926bp SEQ ID No: 2

| Sequence | Position |
|---|---|
| AAACTTCTCCCAGAATACCCAGGCGTCCTCTCTGAGGTCCAGGAGGAAAAAGGCATCAAG | 3240 |
| TATAAGTTTGAAGTCTACGAGAAGAAAGACTAACAGGAAGATGCTTTCAAGTTCTCTGCT | 3300 |
| CCCCTCCTAAAGCTATGCATTTTTATAAGACCATGCTAGCTTGAACTTGTTTATTGCAGC | 3360 |
| TTATAATGGTTACAAATAAAGCAATAGCATCACAAATTTCACAAATAAAGCATTTTTTTC | 3420 |
| ACTGCATTCTAGTTGTGGTTTGTCCAAACTCATCAATGTATCTTATCATGTCTGGATCAA | 3480 |
| CGATAGCTTATCTGTGGGCGATGCCAAGCACCTGGATGCTGTTGGTTTCCTGCTACTGAT | 3540 |
| TTAGAAGCCATTTGCCCCCTGAGTGGGGCTTGGGAGCACTAACTTTCTCTTTCAAAGGAA | 3600 |
| GCAATGCAGAAAGAAAAGCATACAAAGTATAAGCTGCCATGTAATAATGGAAGAAGATAA | 3660 |
| GGTTGTATGAATTAGATTTACATACTTCTGAATTGAAACTAAACACCTTTAAATTCTTAA | 3720 |
| ATATATAACACATTTCATATGAAAGTATTTTACATAAGTAACTCAGATACATAGAAAACA | 3780 |
| AAGCTAATGATAGGTGTCCCTAAAAGTTCATTTATTAATTCTACAAATGATGAGCTGGCC | 3840 |
| ATCAAAATTCCAGCTCAATTCTTCAACGAATTAGAAAGAGCAATCTGCAAACTCATCTGG | 3900 |
| AATAACAAAAAACCTAGGATAGCAAAAACTCTTCTCAAGGATAAAAGAACCTCTGGTGGA | 3960 |
| ATCACCATGCCTGACCTAAAGCTGTACTACAGAGCAATTGTGATAAAAACTGCATGGTAC | 4020 |
| TGATATAGAAACGGACAAGTAGACCAATGGAATAGAACCCACACACCTATGGTCACTTGA | 4080 |
| TCTTCAACAAGAGAGCTAAAACCATCCACTGGAAAAAAGACAGCATTTTCAACAAATGGT | 4140 |
| GCTGGCACAACTGGTGGTTATCATGGAGAAGAATGTGAATTGATCCATTCCAATCTCCTT | 4200 |
| GTACTAAGGTCAAATCTAAGTGGATCAAGGAACTCCACATAAAACCAGAGACACTGAAAC | 4260 |
| TTATAGAGGAGAAAGTGGGGAAAAGCCTCGAAGATATGGGCACAGGGGAAAAATTCCTGA | 4320 |
| ATAGAACAGCAATGGCTTGTGCTGTAAGATCGAGAATTGACAAATGGGACCTCATGAAAC | 4380 |
| TCCAAAGCTATCGGATCAATTCCTCCAAAAAAGCCTCCTCACTACTTCTGGAATAGCTCA | 4440 |
| GAGGCCGAGGCGGCCTCGGCCTCTGCATAAATAAAAAAAATTAGTCAGCCATGCATGGGG | 4500 |
| CGGAGAATGGGCGGAACTGGGCGGAGTTAGGGGCGGGATGGGCGGAGTTAGGGGCGGGAC | 4560 |
| TATGGTTGCTGACTAATTGAGATGCATGCTTTGCATACTTCTGCCTGCTGGGGAGCCTGG | 4620 |
| GGACTTTCCACACCTGGTTGCTGACTAATTGAGATGCATGCTTTGCATACTTCTGCCTGC | 4680 |
| TGGGGAGCCTGGGGACTTTCCACACCCTAACTGACACACATTCCACAGAATTAATTCCCG | 4740 |
| ATCCCGTCGACCTCGAGAGCTTGGCGTAATCATGGTCATAGCTGTTTCCTGTGTGAAATT | 4800 |
| GTTATCCGCTCACAATTCCACACAACATACGAGCCGGAAGCATAAAGTGTAAAGCCTGGG | 4860 |
| GTGCCTAATGAGTGAGCTAACTCACATTAATTGCGTTGCGCTCACTGCCCGCTTTCCAGT | 4920 |
| CGGGAAACCTGTCGTGCCAGCTGCATTAATGAATCGGCCAACGCGCGGGGAGAGGCGGTT | 4980 |
| TGCGTATTGGGCGCTCTTCCGCTTCCTCGCTCACTGACTCGCTGCGCTCGGTCGTTCGGC | 5040 |
| TGCGGCGAGCGGTATCAGCTCACTCAAAGGCGGTAATACGGTTATCCACAGAATCAGGGG | 5100 |
| ATAACGCAGGAAAGAACATGTGAGCAAAAGGCCAGCAAAAGGCCAGGAACCGTAAAAAGG | 5160 |
| CCGCGTTGCTGGCGTTTTTCCATAGGCTCCGCCCCCCTGACGAGCATCACAAAAATCGAC | 5220 |
| GCTCAAGTCAGAGGTGGCGAAACCCGACAGGACTATAAAGATACCAGGCGTTTCCCCCTG | 5280 |
| GAAGCTCCCTCGTGCGCTCTCCTGTTCCGACCCTGCCGCTTACCGGATACCTGTCCGCCT | 5340 |
| TTCTCCCTTCGGGAAGCGTGGCGCTTTCTCAATGCTCACGCTGTAGGTATCTCAGTTCGG | 5400 |
| TGTAGGTCGTTCGCTCCAAGCTGGGCTGTGTGCACGAACCCCCCGTTCAGCCCGACCGCT | 5460 |
| GCGCCTTATCCGGTAACTATCGTCTTGAGTCCAACCCGGTAAGACACGACTTATCGCCAC | 5520 |
| TGGCAGCAGCCACTGGTAACAGGATTAGCAGAGCGAGGTATGTAGGCGGTGCTACAGAGT | 5580 |
| TCTTGAAGTGGTGGCCTAACTACGGCTACACTAGAAGGACAGTATTTGGTATCTGCGCTC | 5640 |
| TGCTGAAGCCAGTTACCTTCGGAAAAAGAGTTGGTAGCTCTTGATCCGGCAAACAAACCA | 5700 |
| CCGCTGGTAGCGGTGGTTTTTTTGTTTGCAAGCAGCAGATTACGCGCAGAAAAAAAGGAT | 5760 |
| CTCAAGAAGATCCTTTGATCTTTTCTACGGGGTCTGACGCTCAGTGGAACGAAAACTCAC | 5820 |
| GTTAAGGGATTTTGGTCATGAGATTATCAAAAAGGATCTTCACCTAGATCCTTTTAAATT | 5880 |
| AAAAATGAAGTTTTAAATCAATCTAAAGTATATATGAGTAAACTTGGTCTGACAGTTACC | 5940 |
| AATGCTTAATCAGTGAGGCACCTATCTCAGCGATCTGTCTATTTCGTTCATCCATAGTTG | 6000 |
| CCTGACTCCCCGTCGTGTAGATAACTACGATACGGGAGGGCTTACCATCTGGCCCCAGTG | 6060 |
| CTGCAATGATACCGCGAGACCCACGCTCACCGGCTCCAGATTTATCAGCAATAAACCAGC | 6120 |
| CAGCCGGAAGGGCCGAGCGCAGAAGTGGTCCTGCAACTTTATCCGCCTCCATCCAGTCTA | 6180 |
| TTAATTGTTGCCGGGAAGCTAGAGTAAGTAGTTCGCCAGTTAATAGTTTGCGCAACGTTG | 6240 |
| TTGCCATTGCTACAGGCATCGTGGTGTCACGCTCGTCGTTTGGTATGGCTTCATTCAGCT | 6300 |
| CCGGTTCCCAACGATCAAGGCGAGTTACATGATCCCCCATGTTGTGCAAAAAAGCGGTTA | 6360 |
| GCTCCTTCGGTCCTCCGATCGTTGTCAGAAGTAAGTTGGCCGCAGTGTTATCACTCATGG | 6420 |
| TTATGGCAGCACTGCATAATTCTCTTACTGTCATGCCATCCGTAAGATGCTTTTCTGTGA | 6480 |
| CTGGTGAGTACTCAACCAAGTCATTCTGAGAATAGTGTATGCGGCGACCGAGTTGCTCTT | 6540 |
| GCCCGGCGTCAATACGGGATAATACCGCGCCACATAGCAGAACTTTAAAAGTGCTCATCA | 6600 |
| TTGGAAAACGTTCTTCGGGGCGAAAACTCTCAAGGATCTTACCGCTGTTGAGATCCAGTT | 6660 |
| CGATGTAACCCACTCGTGCACCCAACTGATCTTCAGCATCTTTTACTTTCACCAGCGTTT | 6720 |
| CTGGGTGAGCAAAAACAGGAAGGCAAAATGCCGCAAAAAAGGGAATAAGGGCGACACGGA | 6780 |
| AATGTTGAATACTCATACTCTTCCTTTTTCAATATTATTGAAGCATTTATCAGGGTTATT | 6840 |
| GTCTCATGAGCGGATACATATTTGAATGTATTTAGAAAAATAAACAAATAGGGGTTCCGC | 6900 |
| GCACATTTCCCCGAAAAGTGCCACCT | 6926 |

TABLE 3

DNA sequence of IL4.Y124D/IgG1 fusion molecule coding region, 1164bp

SEQ ID No: 3

| Sequence | Position |
|---|---|
| ATGGGTCTCACCTCCCAACTGCTTCCCCCTCTGTTCTTCCTGCTAGCATGTGCCGGCAAC | 60 |
| TTTGTCCACGGACACAAGTGCGATATCACCTTACAGGAGATCATCAAAACTTTGAACAGC | 120 |

TABLE 3-continued

DNA sequence of IL4.Y124D/IgG1 fusion molecule coding region, 1164bp

SEQ ID No: 3

| | |
|---|---|
| CTCACAGAGCAGAAGACTCTGTGCACCGAGTTGACCGTAACAGACATCTTTGCTGCCTCC | 180 |
| AAGAACACAACTGAGAAGGAAACCTTCTGCAGGGCTGCGACTGTGCTCCGGCAGTTCTAC | 240 |
| AGCCACCATGAGAAGGACACTCGCTGCCTGGGTGCGACTGCACAGCAGTTCCACAGGCAC | 300 |
| AAGCAGCTGATCCGATTCCTGAAACGGCTCGACAGGAACCTCTGGGGCCTGGCGGGCTTG | 360 |
| AATTCCTGTCCTGTGAAGGAAGCCAACCAGAGTACGTTGGAAAACTTCTTGGAAAGGCTA | 420 |
| AAGACGATCATGAGAGAGAAAGACTCAAAGTGTTCGAGCGGTACCGAGCCCAAATCGGCC | 480 |
| GACAAAACTCACACATGCCCACCGTGCCCAGCACCTGAACTCCTGGGGGGACCGTCAGTC | 540 |
| TTCCTCTTCCCCCCAAAACCCAAGGACACCCTCATGATCTCCCGGACCCCTGAGGTCACA | 600 |
| TGCGTGGTGGTGGACGTGAGCCACGAAGACCCTGAGGTCAAGTTCAACTGGTACGTGGAC | 660 |
| GGCGTGGAGGTGCATAATGCCAAGACAAAGCCGCGGGAGGAGCAGTACAACAGCACGTAC | 720 |
| CGGGTGGTCAGCGTCCTCACCGTCCTGCACCAGGACTGGCTGAATGGCAAGGAGTACAAG | 780 |
| TGCAAGGTCTCCAACAAAGCCCTCCCAGCCCCCATCGAGAAAACCATCTCCAAAGCCAAA | 840 |
| GGGCAGCCCCGAGAACCACAGGTGTACACCCTGCCCCCATCCCGGGATGAGCTGACCAAG | 900 |
| AACCAGGTCAGCCTGACCTGCCTGGTCAAAGGCTTCTATCCCAGCGACATCGCCGTGGAG | 960 |
| TGGGAGAGCAATGGGCAGCCGGAGAACAACTACAAGACCACGCCTCCCGTGCTGGACTCC | 1020 |
| GACGGCTCCTTCTTCCTCTACAGCAAGCTCACCGTGGACAAGAGCAGGTGGCAGCAGGGG | 1080 |
| AACGTCTTCTCATGCTCCGTGATGCATGAGGCTCTGCACAACCACTACACGCAGAAGAGC | 1140 |
| CTCTCCCTGTCTCCGGGTAAATGA | 1164 |

TABLE 4

Sequence of encoded IL4.Y124D/IgG1 fusion protein, 387aa

SEQ ID No: 4

| | | | | |
|---|---|---|---|---|
| 1 MGLTSQLLPP | LFFLLACAGN | FVHGHKCDIT | LQEIIKTLNS | LTEQKTLCTE |
| 51 LTVTDIFAAS | KNTTEKETFC | RAATVLRQFY | SHHEKDTRCL | GATAQQFHRH |
| 101 KQLIRFLKRL | DRNLWGLAGL | NSCPVKEANQ | STLENFLERL | KTIMREKDSK |
| 151 CSSGTEPKSA | DKTHTCPPCP | APELLGGPSV | FLFPPKPKDT | LMISRTPEVT |
| 201 CVVVDVSHED | PEVKFNWYVD | GVEVHNAKTK | PREEQYNSTY | RVVSVLTVLH |
| 251 QDWLNGKEYK | CKVSNKALPA | PIEKTISKAK | GQPREPQVYT | LPPSRDELTK |
| 301 NQVSLTCLVK | GFYPSDIAVE | WESNGQPENN | YKTTPPVLDS | DGSFFLYSKL |
| 351 TVDKSRWQQG | NVFSCSVMHE | ALHNHYTQKS | LSLSPGK* | |

TABLE 5

DNA sequence of synthetic IgG4 cDNA, 1006bp

SEQ ID No: 5

| | |
|---|---|
| GCTTCCACCAAGGGCCCATCCGTCTTCCCCCTGGCGCCCTGCTCCAGGAGCACCTCCGAG | 60 |
| AGCACAGCCGCCCTGGGCTGCCTGGTCAAGGACTACTTCCCCGAACCGGTGACGGTGTCG | 120 |
| TGGAACTCAGGCGCCCTGACCAGCGGCGTGCACACCTTCCCGGCTGTCCTACAGTCCTCA | 180 |
| GGACTCTACTCCCTCAGCAGCGTGGTGACCGTGCCCTCCAGCAGCTTGGGCACGAAGACC | 240 |
| TACACCTGCAACGTAGATCACAAGCCCAGCAACACCAAGGTGGACAAGAGAGTTGAGTCC | 300 |
| AAATATGGTCCCCCATGCCCATCATGCCCAGCACCTGAATTTCTGGGGGGACCATCAGTC | 360 |
| TTCCTGTTCCCCCCAAAACCCAAGGACACTCTCATGATCTCCCGGACCCCTGAGGTCACG | 420 |
| TGCGTGGTGGTGGACGTGAGCCAGGAAGACCCCGAGGTCCAGTTCAACTGGTACGTGGAT | 480 |
| GGCGTGGAGGTGCATAATGCCAAGACAAAGCCGCGGGAGGAGCAGTTCAACAGCACGTAC | 540 |
| CGTGTGGTCAGCGTCCTCACCGTCCTGCACCAGGACTGGCTGAACGGCAAGGAGTACAAG | 600 |
| TGCAAGGTCTCCAACAAAGGCCTCCCGTCATCGATCGAGAAAACCATCTCCAAAGCCAAA | 660 |
| GGGCAGCCCCGAGAGCCACAGGTGTACACCCTGCCCCCATCCCAGGAGGAGATGACCAAG | 720 |
| AACCAGGTCAGCCTGACCTGCCTGGTCAAAGGCTTCTACCCCAGCGACATCGCCGTGGAG | 780 |
| TGGGAGAGCAATGGGCAGCCGGAGAACAACTACAAGACCACGCCTCCCGTGCTGGACTGG | 840 |
| GACGGATCCTTCTTCCTCTACAGCAGGCTAACCGTGGACAAGAGCAGGTGGCAGGAGGGG | 900 |
| AATGTCTTCTCATGCTCCGTGATGCATGAGGCTCTGCACAACCACTACACACAGAAGAGC | 960 |
| CTCTCCCTGTCTCTGGGTAAATGAGTGTAGTCTAGATCTACGTATG | 1006 |

TABLE 6

DNA sequence of IL4.Y124D/IgG4 fusion molecule coding region, 1149bp

SEQ ID No: 6

| | |
|---|---|
| ATGGGTCTCACCTCCCAACTGCTTCCCCCTCTGTTCTTCCTGCTAGCATGTGCCGGCAAC | 60 |
| TTTGTCCACGGACACAAGTGCGATATCACCTTACAGGAGATCATCAAAACTTTGAACAGC | 120 |
| CTCACAGAGCAGAAGACTCTGTGCACCGAGTTGACCGTAACAGACATCTTTGCTGCCTCC | 180 |
| AAGAACACAACTGAGAAGGAAACCTTCTGCAGGGCTGCGACTGTGCTCCGGCAGTTCTAC | 240 |

TABLE 6-continued

DNA sequence of IL4.Y124D/IgG4 fusion molecule coding region, 1149bp

SEQ ID No: 6

| Sequence | Position |
|---|---|
| AGCCACCATGAGAAGGACACTCGCTGCCTGGGTGCGACTGCACAGCAGTTCCACAGGCAC | 300 |
| AAGCAGCTGATCCGATTCCTGAAACGGCTCGACAGGAACCTCTGGGGCCTGGCGGGCTTG | 360 |
| AATTCCTGTCCTGTGAAGGAAGCCAACCAGAGTACGTTGGAAAACTTCTTGGAAAGGCTA | 420 |
| AAGACGATCATGAGAGAGAAAGACTCAAAGTGCTCGAGCGAGTCCAAATATGGTCCCCCG | 480 |
| TGCCCATCATGCCCAGCACCTGAATTTCTGGGGGGACCATCAGTCTTCCTGTTCCCCCCA | 540 |
| AAACCCAAGGACACTCTCATGATCTCCCGGACCCCTGAGGTCACGTGCGTGGTGGTGGAC | 600 |
| GTGAGCCAGGAAGACCCCGAGGTCCAGTTCAACTGGTACGTGGATGGCGTGGAGGTGCAT | 660 |
| AATGCCAAGACAAAGCCGCGGGAGGAGCAGTTCAACAGCACGTACCGTGTGGTCAGCGTC | 720 |
| CTCACCGTCCTGCACCAGGACTGGCTGAACGGCAAGGAGTACAAGTGCAAGGTCTCCAAC | 780 |
| AAAGGCCTCCCGTCATCGATCGAGAAAACCATCTCCAAAGCCAAAGGGCAGCCCCGAGAG | 840 |
| CCACAGGTGTACACCCTGCCCCCATCCCAGGAGGAGATGACCAAGAACCAGGTCAGCCTG | 900 |
| ACCTGCCTGGTCAAAGGCTTCTACCCCAGCGACATCGCCGTGGAGTGGGAGAGCAATGGG | 960 |
| CAGCCGGAGAACAACTACAAGACCACGCCTCCCGTGCTGGACTCCGACGGATCCTTCTTC | 1020 |
| CTCTACAGCAGGCTAACCGTGGACAAGAGCAGGTGGCAGGAGGGGAATGTCTTCTCATGC | 1080 |
| TCCGTGATGCATGAGGCTCTGCACAACCACTACACACAGAAGAGCCTCTCCCTGTCTCTG | 1140 |
| GGTAAATGA | 1149 |

TABLE 7

Sequence of encoded IL4.Y124D/IgG4 fusion protein, 382aa

SEQ ID No: 7

| | | | | |
|---|---|---|---|---|
| 1 MGLTSQLLPP | LFFLLACAGN | FVHGHKCDIT | LQEIIKTLNS | LTEQKTLCTE |
| 51 LTVTDIFAAS | KNTTEKETFC | RAATVLRQFY | SHHEKDTRCL | GATAQQFHRH |
| 101 KQLIRFLKRL | DRNLWGLAGL | NSCPVKEANQ | STLENFLERL | KTIMREKDSK |
| 151 CSSESKYGPP | CPSCPAPEFL | GGPSVFLFPP | KPKDTLMISR | TPEVTCVVVD |
| 201 VSQEDPEVQF | NWYVDGVEVH | NAKTKPREEQ | FNSTYRVVSV | LTVLHQDWLN |
| 251 GKEYKCKVSN | KGLPSSIEKT | ISKAKGQPRE | PQVYTLPPSQ | EEMTKNQVSL |
| 301 TCLVKGFYPS | DIAVEWESNG | QPENNYKTTP | PVLDSDGSFF | LYSRLTVDKS |
| 351 RWQEGNVFSC | SVMHEALHNH | YTQKSLSLSL | GK* | |

TABLE 8

DNA sequence of IgG4 PE variant, 984bp

SEQ ID No: 8

| Sequence | Position |
|---|---|
| GCTAGTACCAAGGGCCCATCCGTCTTCCCCCTGGCGCCCTGCTCCAGGAGCACCTCCGAG | 60 |
| AGCACgGCCGCCCTGGGCTGCCTGGTCAAGGACTACTTCCCCGAACCGGTGACGGTGTCG | 120 |
| TGGAACTCAGGCGCCCTGACCAGCGGCGTGCACACCTTCCCGGCTGTCCTACAGTCCTCA | 180 |
| GGACTCTACTCCCTCAGCAGCGTGGTGACCGTGCCCTCCAGCAGCTTGGGCACGAAGACC | 240 |
| TACACCTGCAACGTAGATCACAAGCCCAGCAACACCAAGGTGGACAAGAGAGTTGAGTCC | 300 |
| AAATATGGTCCCCCATGCCCAcCATGCCCAGCgCCTGAaTTtgaGGGGGGACCATCAGTC | 360 |
| TTCCTGTTCCCCCCAAAACCCAAGGACACTCTCATGATCTCCCGGACCCCTGAGGTCACG | 420 |
| TGCGTGGTGGTGGACGTGAGCCAGGAAGACCCCGAGGTCCAGTTCAACTGGTACGTGGAT | 480 |
| GGCGTGGAGGTGCATAATGCCAAGACAAAGCCGCGGGAGGAGCAGTTCAACAGCACGTAC | 540 |
| CGTGTGGTCAGCGTCCTCACCGTCCTGCACCAGGACTGGCTGAACGGCAAGGAGTACAAG | 600 |
| TGCAAGGTCTCCAACAAAGGCCTCCCGTCaTCgATCGAGAAAACCATCTCCAAAGCCAAA | 660 |
| GGGCAGCCCCGAGAGCCACAGGTGTACACCCTGCCCCCATCCCAGGAGGAGATGACCAAG | 720 |
| AACCAGGTCAGCCTGACCTGCCTGGTCAAAGGCTTCTACCCCAGCGACATCGCCGTGGAG | 780 |
| TGGGAGAGCAATGGGCAGCCGGAGAACAACTACAAGACCACGCCTCCCGTGCTGGACTCC | 840 |
| GACGGaTCCTTCTTCCTCTACAGCAGGCTAACCGTGGACAAGAGCAGGTGGCAGGAGGGG | 900 |
| AATGTCTTCTCATGCTCCGTGATGCATGAGGCTCTGCACAACCACTACACACAGAAGAGC | 960 |
| CTCTCCCTGTCTCTGGGTAAATGA | 984 |

TABLE 9

DNA sequence of IL4.Y124D/IgG4 PE fusion molecule coding region, 1149bp

SEQ ID No: 9

| Sequence | Position |
|---|---|
| ATGGGTCTCACCTCCCAACTGCTTCCCCCTCTGTTCTTCCTGCTAGCATGTGCCGGCAAC | 60 |
| TTTGTCCACGGACACAAGTGCGATATCACCTTACAGGAGATCATCAAAACTTTGAACAGC | 120 |
| CTCACAGAGCAGAAGACTCTGTGCACCGAGTTGACCGTAACAGACATCTTTGCTGCCTCC | 180 |
| AAGAACACAACTGAGAAGGAAACCTTCTGCAGGGCTGCGACTGTGCTCCGGCAGTTCTAC | 240 |
| AGCCACCATGAGAAGGACACTCGCTGCCTGGGTGCGACTGCACAGCAGTTCCACAGGCAC | 300 |
| AAGCAGCTGATCCGATTCCTGAAACGGCTCGACAGGAACCTCTGGGGCCTGGCGGGCTTG | 360 |

TABLE 9-continued

DNA sequence of IL4.Y124D/IgG4 PE fusion molecule coding region, 1149bp

SEQ ID No: 9

| | |
|---|---|
| AATTCCTGTCCTGTGAAGGAAGCCAACCAGAGTACGTTGGAAAACTTCTTGGAAAGGCTA | 420 |
| AAGACGATCATGAGAGAGAAAGACTCAAAGTGCTCGAGCGAGTCCAAATATGGTCCCCCA | 480 |
| TGCCCACCATGCCCAGCgCCTGAATTTGAGGGGGGACCATCAGTCTTCCTGTTCCCCCCA | 540 |
| AAACCCAAGGACACTCTCATGATCTCCCGGACCCCTGAGGTCACGTGCGTGGTGGTGGAC | 600 |
| GTGAGCCAGGAAGACCCCGAGGTCCAGTTCAACTGGTACGTGGATGGCGTGGAGGTGCAT | 660 |
| AATGCCAAGACAAAGCCGCGGGAGGAGCAGTTCAACAGCACGTACCGTGTGGTCAGCGTC | 720 |
| CTCACCGTCCTGCACCAGGACTGGCTGAACGGCAAGGAGTACAAGTGCAAGGTCTCCAAC | 780 |
| AAAGGCCTCCCGTCaTCgATCGAGAAAACCATCTCCAAAGCCAAAGGGCAGCCCCGAGAG | 840 |
| CCACAGGTGTACACCCTGCCCCCATCCCAGGAGGAGATGACCAAGAACCAGGTCAGCCTG | 900 |
| ACCTGCCTGGTCAAAGGCTTCTACCCCAGCGACATCGCCGTGGAGTGGGAGAGCAATGGG | 960 |
| CAGCCGGAGAACAACTACAAGACCACGCCTCCCGTGCTGGACTGGGACGGaTCCTTCTTC | 1020 |
| CTCTACAGCAGGCTAACCGTGGACAAGAGCAGGTGGCAGGAGGGGAATGTCTTCTCATGC | 1080 |
| TCCGTGATGCATGAGGCTCTGCACAACCACTACACACAGAAGAGCCTCTCCCTGTCTCTG | 1140 |
| GGTAAATGA | 1149 |

TABLE 10

Sequence of encoded IL4.Y124D/IgG4 PE variant fusion protein, 382aa

SEQ ID No: 10

| | | | | | |
|---|---|---|---|---|---|
| 1 | MGLTSQLLPP | LFFLLACAGN | FVHGHKCDIT | LQEIIKTLNS | LTEQKTLCTE |
| 51 | LTVTDIFAAS | KNTTEKETFC | RAATVLRQFY | SHHEKDTRCL | GATAQQFHRH |
| 101 | KQLIRFLKRL | DRNLWGLAGL | NSCPVKEANQ | STLENFLERL | KTIMREKDSK |
| 151 | CSSESKYGPP | CPPCPAPEFE | GGPSVFLFPP | KPKDTLMISR | TPEVTCVVVD |
| 201 | VSQEDPEVQF | NWYVDGVEVH | NAKTKPREEQ | FNSTYRVVSV | LTVLHQDWLN |
| 251 | GKEYKCKVSN | KGLPSSIEKT | ISKAKGQPRE | PQVYTLPPSQ | EEMTKNQVSL |
| 301 | TCLVKGFYPS | DIAVEWESNG | QPENNYKTTP | PVLDSDGSFF | LYSRLTVDKS |
| 351 | RWQEGNVFSC | SVMHEALHNH | YTQKSLSLSL | GK* | |

We claim:

1. A method of treating a patient suffering from a disease selected from the group consisting of an allergic disease, a T-cell mediated disease and a disease associated with an undesired immune response to an infectious agent, said method comprising the step of:

administering to said patient a therapeutically effective amount of a compound comprising an IL4 mutant or variant in which at least one amino acid at positions 120 to 128 inclusive is different from the amino acid naturally occurring in wild type IL4 fused to at least one human immunoglobulin constant domain.

2. The method according to claim 1 wherein tyrosine naturally occurring at position 124 is replaced with a different amino acid.

3. The method according to claim 1 wherein tyrosine naturally occurring at position 124 is replaced with aspartic acid.

4. The method according to claim 1 wherein said immunoglobulin is of the IgG subclass.

5. The method according to claim 1 wherein said constant domain is the whole or a substantial part of the constant region of the heavy chain of human IgG.

6. The method according to claim 1 wherein said constant domain is the whole or a substantial part of the constant region of the heavy chain of human IgG4.

7. The method according to claim 6 wherein said disease is selected from the group consisting of asthma, rhinitis, conjunctivitis, atopic dermatitis and anaphylaxis.

8. A method of treating a patient suffering from a disease selected from the group consisting of an allergic disease, a T-cell mediated disease and a disease associated with an undesired immune response to an infectious agent, wherein said method comprises the step of:

administering to said patient a therapeutically effective amount of a compound comprising a protein comprising an amino acid sequence selected from the group consisting of SEQ ID NO. 4, SEQ ID NO. 7 and SEQ ID NO. 10.

9. The method according to claim 8 wherein said disease is selected from the group consisting of asthma, rhinitis, conjunctivitis, atopic dermatitis and anaphylaxis.

* * * * *